(12) United States Patent
Kameyama et al.

(10) Patent No.: US 8,465,289 B2
(45) Date of Patent: Jun. 18, 2013

(54) TRAINING ASSISTING APPARATUS, TRAINING ASSISTING METHOD, AND TRAINING ASSISTING PROGRAM STORED ON A COMPUTER READABLE MEDIUM

(75) Inventors: Hirokazu Kameyama, Kanagawa (JP); Shuji Ono, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1042 days.

(21) Appl. No.: 12/294,933

(22) PCT Filed: Mar. 26, 2007

(86) PCT No.: PCT/JP2007/057333
§ 371 (c)(1), (2), (4) Date: Jan. 15, 2009

(87) PCT Pub. No.: WO2007/114404
PCT Pub. Date: Oct. 11, 2007

(65) Prior Publication Data
US 2010/0178639 A1  Jul. 15, 2010

(30) Foreign Application Priority Data

Mar. 28, 2006 (JP) ................................. 2006-088618
Feb. 8, 2007 (JP) ................................. 2007-029093

(51) Int. Cl.
  *G09B 19/00* (2006.01)
(52) U.S. Cl.
  USPC ........................................................ 434/236
(58) Field of Classification Search
  USPC .... 434/236, 307 R, 323, 350; 600/545; 607/2
  See application file for complete search history.

(56) References Cited

U.S. PATENT DOCUMENTS 5,487,665 A * 1/1996 Lechner et al. .................. 434/44
6,012,926 A * 1/2000 Hodges et al. ................ 434/236

(Continued)

FOREIGN PATENT DOCUMENTS

| JP | 09-313611 A | 12/1997 |
| JP | 10-153946 A | 6/1998 |
| JP | 11-155955 A | 6/1999 |

OTHER PUBLICATIONS

International Search Report for corresponding Intern'l Application No. PCT/JP2007/057333, mailed May 1, 2007, 1 page.

(Continued)

*Primary Examiner* — Xuan Thai
*Assistant Examiner* — Peter Egloff
(74) *Attorney, Agent, or Firm* — Sughrue Mion, PLLC

(57) ABSTRACT

An examinee is subjected to an image or a sound suitable for the examinee's overcoming his worries in accordance with change in a physical state of the examinee. The training assisting apparatus according to the present invention is at training assisting apparatus for assisting an examinee in overcoming the examinee's worries by displaying a training image, including: a display section that displays the training image; a display ratio storage section that stores a change quantity of a display ratio of the training image displayed on the display section, in association with a physical state of the examinee; a physical state acquiring section that acquires the physical state of the examinee looking at the training image displayed on the display section; a display ratio extraction section that extracts the change quantity of the display ratio of the training image stored in the display ratio storage section in association with the physical state of the examinee acquired by the physical state acquiring section; and a display control section that changes the display ratio of the training image displayed on the display section, in accordance with the display ratio of the training image extracted by the display ratio extraction section.

13 Claims, 11 Drawing Sheets

U.S. PATENT DOCUMENTS

| | | | |
|---|---|---|---|
| 6,123,661 A | 9/2000 | Fukushima et al. | |
| 6,677,969 B1 | 1/2004 | Hongo | |
| 7,128,577 B2 * | 10/2006 | Renaud | 434/236 |
| 7,130,447 B2 * | 10/2006 | Aughey et al. | 382/103 |

OTHER PUBLICATIONS

Chinese Office Action, dated Nov. 1, 2010, issued in corresponding CN Application No. 200780019671.0 along with letter of Nov. 23, 2010, from Chinese agent with partial translation of Office Action, 16 pages in English and Chinese.

Decision of Rejection, dated Apr. 5, 2012, issued in corresponding CN Application No. 200780019671.0, 28 pages in English and Chinese.

Notification of Reasons for Refusal, dated Jun. 19, 2012, issued in related JP Application No. 2010-186655, 3 pages in English and Japanese.

* cited by examiner

130

| PHYSICAL STATE | | CHANGE QUANTITY OF INFORMATION QUANTITY | | |
|---|---|---|---|---|
| ITEM | MOTION OF PATIENT | TONE | RESOLUTION | ...... |
| CHANGE IN EXPRESSION | CLOSING THE EYES | −4 BIT | ⋮ | ⋮ |
| | TURNING THE EYES AWAY | −2 BIT | ⋮ | ⋮ |
| | SMILING FACE | +6 BIT | ⋮ | ⋮ |
| | ⋮ | ⋮ | ⋮ | ⋮ |
| MOTION | LURCHING | −1 BIT | ⋮ | ⋮ |
| | LOOKING DOWN | −2 BIT | ⋮ | ⋮ |
| | SHAKING THE HEAD | −6 BIT | ⋮ | ⋮ |
| | ⋮ | ⋮ | ⋮ | ⋮ |
| ⋮ | ⋮ | ⋮ | ⋮ | ⋮ |

| PHYSICAL STATE | CHANGE QUANTITY OF INFORMATION QUANTITY | | |
|---|---|---|---|
| BIOLOGICAL INFORMATION | TONE | RESOLUTION | ...... |
| PERSPIRATION | −4 BIT | ⋮ | ⋮ |
| NON-PERSPIRATION | +6 BIT | ⋮ | ⋮ |
| THE BLOOD PRESSURE EXCEEDING A PREDETERMINED VALUE | −6 BIT | ⋮ | ⋮ |
| ⋮ | ⋮ | ⋮ | ⋮ |

| PHYSICAL STATE | | CHANGE QUANTITY OF INFORMATION QUANTITY | | |
|---|---|---|---|---|
| ITEM | CHANGE QUANTITY PER UNIT TIME | TONE | RESOLUTION | ...... |
| NUMBER OF TIMES OF BLINKS | ⋮ | ⋮ | ⋮ | ⋮ |
| | +50 | −4 BIT | ⋮ | ⋮ |
| | ⋮ | ⋮ | ⋮ | ⋮ |
| | −30 | +6 BIT | ⋮ | ⋮ |
| | ⋮ | ⋮ | ⋮ | ⋮ |
| PUPIL SIZE | ⋮ | ⋮ | ⋮ | ⋮ |
| HEART RATE | ⋮ | ⋮ | ⋮ | ⋮ |
| ⋮ | ⋮ | ⋮ | ⋮ | ⋮ |

| PHYSICAL STATE | | CHANGE QUANTITY OF DISPLAY RATIO | | |
|---|---|---|---|---|
| ITEM | MOTION OF PATIENT | DISPLAY TIME | COMBINATION RATIO | ...... |
| CHANGE IN EXPRESSION | CLOSING THE EYES | -10 | ⋮ | ⋮ |
| | TURNING THE EYES AWAY | -5 | ⋮ | ⋮ |
| | SMILING FACE | +10 | ⋮ | ⋮ |
| | ⋮ | ⋮ | ⋮ | ⋮ |
| MOTION | LURCHING | -2 | ⋮ | ⋮ |
| | LOOKING DOWN | 0 | ⋮ | ⋮ |
| | SHAKING THE HEAD | -4 | ⋮ | ⋮ |
| | ⋮ | ⋮ | ⋮ | ⋮ |
| ⋮ | ⋮ | ⋮ | ⋮ | ⋮ |

| PHYSICAL STATE | CHANGE QUANTITY OF DISPLAY RATIO | | |
|---|---|---|---|
| BIOLOGICAL INFORMATION | DISPLAY TIME | COMBINATION RATIO | ...... |
| PERSPIRATION | -5 | ⋮ | ⋮ |
| NON-PERSPIRATION | +10 | ⋮ | ⋮ |
| THE BLOOD PRESSURE EXCEEDING A PREDETERMINED VALUE | -10 | ⋮ | ⋮ |
| ⋮ | ⋮ | ⋮ | ⋮ |

| PHYSICAL STATE | | CHANGE QUANTITY OF DISPLAY RATIO | | |
|---|---|---|---|---|
| ITEM | CHANGE QUANTITY PER UNIT TIME | DISPLAY TIME | COMBINATION RATIO | ...... |
| NUMBER OF TIMES OF BLINKS | ⋮ | ⋮ | ⋮ | ⋮ |
| | +50 | −10 | ⋮ | ⋮ |
| | ⋮ | ⋮ | ⋮ | ⋮ |
| | −30 | −5 | ⋮ | ⋮ |
| | ⋮ | ⋮ | ⋮ | ⋮ |
| PUPIL SIZE | ⋮ | ⋮ | ⋮ | ⋮ |
| HEART RATE | ⋮ | ⋮ | ⋮ | ⋮ |
| ⋮ | ⋮ | ⋮ | ⋮ | ⋮ |

| PHYSICAL STATE | | CHANGE QUANTITY OF FOLLOWING SPEED |
|---|---|---|
| ITEM | CHANGE QUANTITY PER UNIT TIME | |
| NUMBER OF TIMES OF BLINKS | ⋮ | ⋮ |
| | +50 | COERCIVELY STOPS TO FOLLOW |
| | ⋮ | ⋮ |
| | +30 | −10 |
| | ⋮ | ⋮ |
| | −30 | +10 |
| | ⋮ | ⋮ |
| PUPIL SIZE | ⋮ | ⋮ |
| HEART RATE | ⋮ | ⋮ |
| ⋮ | ⋮ | ⋮ |

*FIG. 10*

TRAINING ASSISTING APPARATUS, TRAINING ASSISTING METHOD, AND TRAINING ASSISTING PROGRAM STORED ON A COMPUTER READABLE MEDIUM

TECHNICAL FIELD

The present invention relates to a training assisting apparatus, a training assisting method, and a training assisting program stored on a computer readable medium. In particular, the present invention relates to a training assisting apparatus, a training assisting method, and a training assisting program stored on a computer readable medium, which display a training image to assist an examinee in overcoming his worries. This patent application incorporates herein by reference the contents of Japanese Patent Applications No. 2006-088618 filed on Mar. 28, 2006 and No. 2007-029093 filed on Feb. 8, 2007, if applicable.

BACKGROUND ART

One example of making a patient overcome his worries is a case of treating a patient suffering from mental illness. Technologies for treating such mental illnesses have been conventionally proposed. A concrete example is a phobia treatment apparatus disclosed in the patent document 1, which includes a relaxation apparatus for facilitating generation of alpha waves for relaxing patients and a virtual reality apparatus for providing a patient with images and sound that the patient has a phobia about. The phobia treatment apparatus disclosed in this patent document 1 treats a phobia of a patient by alternate operation of the relaxation apparatus and the virtual reality apparatus.

[Patent document 1] Japanese Patent Application Publication No. H11-155955

DISCLOSURE OF THE INVENTION

Problems to be Solved by the Invention

However, in the phobia treatment apparatus disclosed in the patent document 1, images and sound to be presented to a patient are predetermined, and so it is impossible to automatically change the images or sound into suitable ones according to the change in biological information of a patient. In addition, the phobia treatment apparatus disclosed in the patent document 1 is designed so that an operator will stop the virtual reality apparatus from presenting the images and sound that the patient has a phobia about, when the fear felt by the patient becomes too hard to bear for him. Subsequently the operator operates the relaxation apparatus to induce generation of alpha waves in the brain waves of the patient. Consequently, there is a possibility that images and sound suitable for treatment of a patient's phobia cannot be automatically presented in response to the psychological state of or fear felt by the patient.

In view of this, the present invention aims to provide a training assisting apparatus, a training assisting method, and a training assisting program stored on a computer readable medium that are able to solve the foregoing problems. This purpose is achieved by combinations of features described in the independent claims. The dependent claims define further advantageous and concrete examples of the present invention.

Means for Solving the Problems

So as to solve the foregoing problems, according to the first aspect of the present invention, there is provided a training assisting apparatus for assisting an examinee in overcoming the examinee's worries by displaying a training image, including: a display section that displays the training image; a display ratio storage section that stores a change quantity of a display ratio of the training image displayed on the display section, in association with a physical state of the examinee; a physical state acquiring section that acquires the physical state of the examinee looking at the training image displayed on the display section; a display ratio extraction section that extracts the change quantity of the display ratio of the training image stored in the display ratio storage section in association with the physical state of the examinee acquired by the physical state acquiring section; and a display control section that changes the display ratio of the training image displayed on the display section, in accordance with the display ratio of the training image extracted by the display ratio extraction section.

In addition, an arrangement is also possible in which the display section displays the training image by inserting the training image to a motion picture that is not a training image; the display ratio storage section stores a change quantity of a display time of the training image displayed on the display section, in association with the physical state of the examinee; the display ratio extraction section extracts the change quantity of the display time of the training image stored in the display ratio storage section in association with the physical state of the examinee acquired by the physical state acquiring section; and the display control section changes the display time of the training image displayed on the display section, in accordance with the change quantity of the display time of the training image extracted by the display ratio extraction section. Further, an arrangement is also possible in which the display section displays a combination of the training image and the non-training image, the display ratio storage section stores a change quantity of a combination ratio of the training image displayed on the display section, in association with the physical state of the examinee; the display ratio extraction section extracts a change quantity of the combination ratio of the training image stored in the display ratio storage section in association with the physical state of the examinee acquired by the physical state acquiring section, and the display control section changes the combination ratio of the training image displayed on the display section, in accordance with the change quantity of the combination ratio of the training image extracted by the display ratio extraction section.

In addition, an arrangement is possible in which the display section displays the training image by superimposing the training image on a non-training image, the display ratio storage section stores a change quantity of a superimposing degree of the training image displayed on the display section, in association with the physical state of the examinee, and the display ratio extraction section extracts a change quantity of the superimposing degree of the training image stored in the display ratio storage section in association with the physical state of the examinee acquired by the physical state acquiring section, and the display control section changes the superimposing degree of the training image displayed on the display section, in accordance with the change quantity of the superimposing degree of the training image extracted by the display ratio extraction section. Further, an arrangement is possible in which the training assisting apparatus further includes: an image-capturing section that captures an image of the examinee looking at the training image displayed on the display section, where the display ratio storage section stores the change quantity of the display ratio of the training image displayed on the display section, in association with a motion of the examinee being the physical state of the examinee, the physical state acquiring section acquires the motion of the examinee, by analyzing the image of the examinee captured by the image-capturing section, and the display ratio extraction section extracts the change quantity of the display ratio of the training image that the display ratio storage section stores in association with the motion of the examinee acquired by the physical state acquiring section.

Further, an arrangement is possible in which the display ratio storage section stores the change quantity of the display ratio of the training image displayed on the display section, in association with a change quantity per unit time of the motion of the examinee, the physical state acquiring section acquires the change quantity per unit time of the motion of the examinee, by analyzing the image of the examinee captured by the image-capturing section, and the display ratio extraction section extracts the change quantity of the display ratio of the training image that the display ratio storage section stores in association with the change quantity per unit time of the motion of the examinee acquired by the physical state acquiring section. Further, an arrangement is possible in which training assisting apparatus further includes: a biological information measurement section that measures biological information of the examinee looking at the training image displayed on the display section, where the display ratio storage section stores the change quantity of the display ratio of the training image displayed on the display section, in association with biological information of the examinee being the physical state of the examinee, the physical state acquiring section acquires the biological information of the examiner measured by the biological information measurement section, and the display ratio extraction section extracts the change quantity of the display ratio of the training image that the display ratio storage section stores in association with the biological information of the examinee acquired by the physical state acquiring section.

Further, an arrangement is possible in which the display ratio storage section stores the change quantity of the display ratio of the training image displayed on the display section, in association with a change quantity per unit time of the biological information of the examinee, the physical state acquiring section acquires the change quantity per unit time of the biological information of the examinee measured by the biological information measurement section, and the display ratio extraction section extracts the display ratio of the training image that the display ratio storage section stores in association with the change quantity per unit time of the biological information of the examinee acquired by the physical state acquiring section. Furthermore, an arrangement is possible in which the training assisting apparatus further includes: a sound playback section that plays back sound that corresponds to the training image displayed on the display section; a sound change quantity storage section that stores a change quantity of an information quantity of the sound played back by the sound playback section, in association with the physical state of the examinee; a sound change quantity extraction section that extracts the change quantity of the information quantity of the sound that the sound change quantity storage section stores in association with the physical state of the examinee acquired by the physical state acquiring section; and a sound change control section that changes the information quantity of the sound played back by the sound playback section, in association with the change quantity of the information quantity of the sound extracted by the sound change quantity extraction section.

Moreover, according to the second aspect of the present invention, there is provided a training assisting method for assisting an examinee in overcoming the examinee's worries by displaying a training image, including: a displaying step of displaying the training image on a display section; a physical state acquiring step of acquiring a physical state of the examinee looking at the training image displayed on the displaying section; a display ratio extraction step of extracting a change quantity of a display ratio of the training image stored in a display ratio storage section in association with the physical state of the examinee acquired in the physical state acquiring step; and a display control step of changing a display ratio of the training image displayed on the display section, in accordance with the display ratio of the training image extracted in the display ratio extraction step.

According to the third aspect of the present invention, there is provided a training assisting program stored on a computer readable medium for a training assisting apparatus that assists an examinee in overcoming the examinee's worries by displaying a training image, the training assisting program stored on a computer readable medium causes the training assisting apparatus to function as: a display section that displays the training image; a display ratio storage section that stores a change quantity of a display ratio of the training image displayed on the display section, in association with a physical state of the examinee; a physical state acquiring section that acquires the physical state of the examinee looking at the training image displayed on the display section; a display ratio extraction section that extracts the change quantity of the display ratio of the training image stored in the display ratio storage section in association with the physical state of the examinee acquired by the physical state acquiring section; and a display control section that changes the display ratio of the training image displayed on the display section, in accordance with the display ratio of the training image extracted by the display ratio extraction section.

According to the fourth aspect of the present invention, there is provided a training assisting apparatus for assisting an examinee in overcoming the examinee's worries by displaying a training image, including: a display section that displays the training image; an image-capturing section that captures an image of the examinee looking at the training image displayed on the display section; an examinee's line-of-sight measurement section that detects a direction of line of sight of the examinee based on the image of the examinee captured by the image-capturing section; and a display control section that controls the display section to display the training image by causing the training image to follow the direction of the line of sight of the examinee measured in the examinee's line-of-sight measurement section.

In addition, an arrangement is possible in which the training assisting apparatus further includes: a physical state acquiring section that acquires a physical state of the examinee looking at the training image displayed on the display section; a following speed change quantity storage section that stores a change quantity of the speed of causing the training image to follow the direction of the line of sight of the examinee, in association with the physical state of the examinee acquired by the physical state acquiring section; and a following speed extraction section that extracts the change quantity of the speed of causing the training image to follow the direction of the line of sight of the examinee that the following speed change quantity storage section stores in association with the physical state of the examinee acquired by the physical state acquiring section, where the display control section controls the display section to display the training image by causing the training image to follow the direction of the line of sight of the examinee, in accordance with the change quantity of the speed of causing the training image to follow extracted by the following speed extraction section.

In addition, an arrangement is possible in which the following speed change quantity storage section stores information indicating to display the training image without moving the training image, in association with a predetermined physical state indicating that the examinee is feeling extraordinary fear, the following speed change quantity extraction section extracts the information indicating to display the training image without moving the training image stored in the following speed change quantity storage section, if the physical state of the examinee acquired by the physical state acquiring section is the predetermined physical state, and the display control section controls the display section to display the training image based on the information indicating to display the training image without moving the training image extracted by the following speed change quantity extraction section.

Moreover, according to the fifth aspect of the present invention, there is provided a training assisting method for assisting an examinee in overcoming the examinee's worries by displaying a training image, including: a display step of displaying the training image on a display section; an image-capturing step of capturing an image of the examinee looking at the training image displayed on the display section; an examinee's line-of-sight measurement step of detecting a direction of line of sight of the examinee based on the image of the examinee captured in the image-capturing step; and a display control step of controlling the display section to display the training image by causing the training image to follow the direction of the line of sight of the examinee measured in the examinee's line-of-sight measurement step.

In addition, according to the sixth aspect of the present invention, there is provided a training assisting program stored on a computer readable medium for a training assisting apparatus that assists an examinee in overcoming the examinee's worries by displaying a training image, the training assisting program stored on a computer readable medium causes the training assisting apparatus to function as: a display section that displays the training image; an image-capturing section that captures an image of the examinee looking at the training image displayed on the display section, an examinee's line-of-sight measurement section that detects a direction of line of sight of the examinee based on the image of the examinee captured by the image-capturing section; and a display control section that controls the display section to display the training image by causing the training image to follow the direction of the line of sight of the examinee.

The summary of the invention does not necessarily describe all necessary features of the present invention. The present invention may also be a sub-combination of the features described above.

Effect of the Invention

According to the present invention, it becomes possible to subject an examinee to such stimulus as images, sound, and the like that are suitable for overcoming his worries, depending on change of the examinee's physical states.

BRIEF DESCRIPTION OF THE DRAWINGS

FIG. 3 is a diagram showing a data structure of an image change quantity storage section 130.

FIG. 4 is a diagram showing a data structure of the image change quantity storage section 130.

FIG. 5 is a diagram showing a data structure of the image change quantity storage section 130.

FIG. 7 is a diagram showing a data structure of a display ratio storage section 132.

FIG. 8 is a diagram showing a data structure of the display ratio storage section 132.

FIG. 9 is a diagram showing a data structure of the display ratio storage section 132.

FIG. 10 is a diagram showing a data structure of a following speed change quantity storage section 138.

BEST MODE FOR CARRYING OUT THE INVENTION

The invention will now be described based on the preferred embodiments, which do not intend to limit the scope of the present invention, but exemplify the invention. All of the features and the combinations thereof described in the embodiment are not necessarily essential to the invention. Furthermore, the following describes the present invention by way of an example of an embodiment in which a training assisting apparatus of the present invention is applied to a mental illness treatment assisting apparatus. However, the application of the training assisting apparatus of the present invention is not limited to treatment of mental illnesses.

Figure 1:
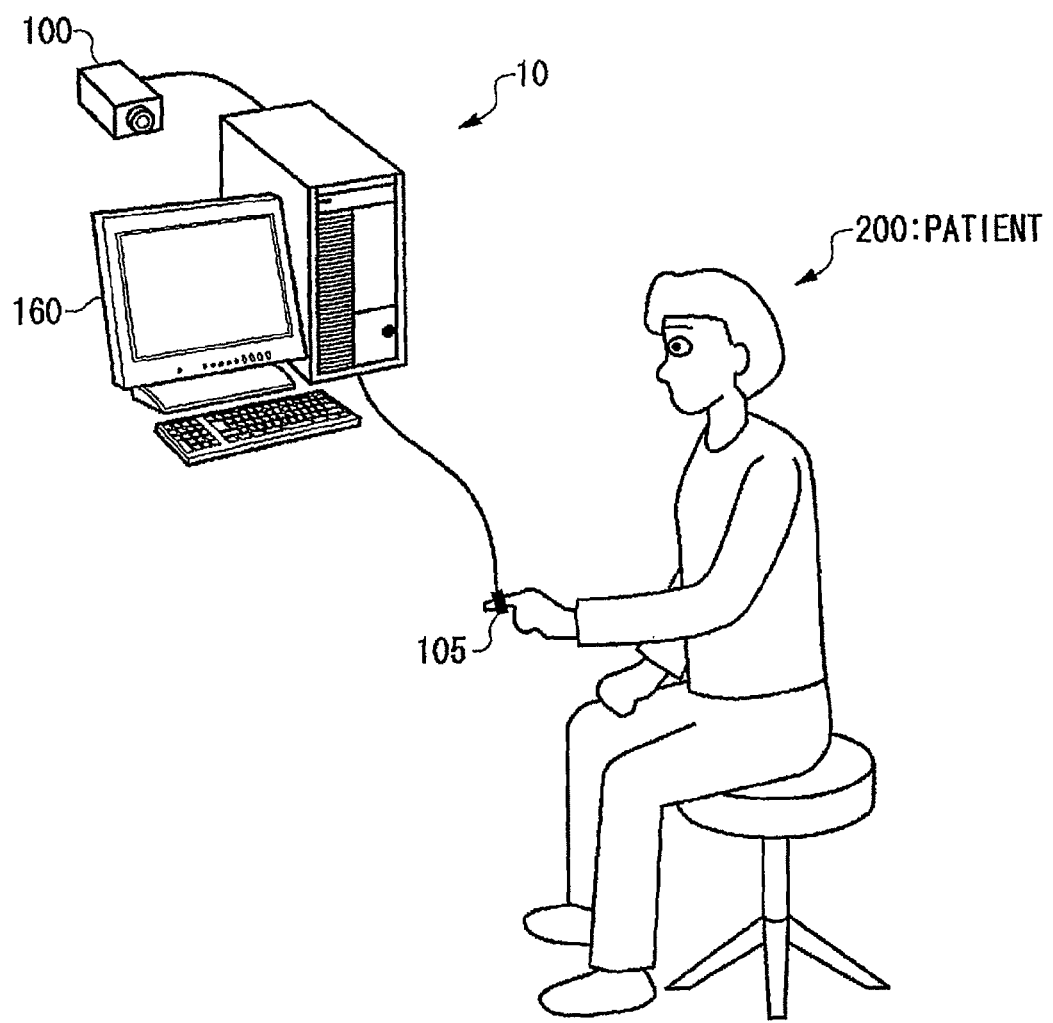
FIG. 1 is a schematic view of a mental illness treatment assisting apparatus 10.

FIG. 1 shows a schematic view of a mental illness treatment assisting apparatus 10 according to one embodiment of the present invention. The mental illness treatment assisting apparatus 10 (hereinafter simply "assisting apparatus 10") includes an image-capturing section 100 for capturing an image of a patient 200, a biological information measurement section 105 for measuring biological information of the patient 200, and a display section 160 for displaying a training image. The assisting apparatus 10 displays, on the display section 160, a training image that induces an unfavorable phobic reaction of the patient 200. The assisting apparatus 10 then changes the information quantity in the training image depending on the physical state of the patient 200, and displays the training image of which the information quantity has been changed, on the display section 160. For example, the information quantity may be resolution, tone, and so on of the training image. The assisting apparatus 10 according to the present embodiment automatically changes the information quantity of the training image depending on the physical state of the patient 200, and subjects the patient 200 to the training image of which the information quantity has been changed, aiming to assist treatment of various phobias such as a panic syndrome, acrophobia, agoraphobia, astraphobia, aviophobia, social phobia, and the like.

For example, the assisting apparatus 10 displays on the display section 160 training images showing spider(s) that differ in type, number, size, and the like depending on the physical state of the patient 200 who has a phobia about spiders. The assisting apparatus 10 may display on the display section 160 training images of animated spider or photographed spider according to the physical state of the patient 200. For example when having judged that there is a possibility that the patient 200 has a panic attack from the measurement result of the biological information measurement section 105, the assisting apparatus 10 displays a training image of an animated spider on the display section 160. On the other hand, when having judged that there is no possibility that the patient 200 has a panic attack, the assisting apparatus 10 displays a training image of a photographed spider on the display section 160.

For a patient 200 having trouble riding on a train due to agoraphobia, the assisting apparatus 10 may also present to the patient 200 by displaying on the display section 160 various training images differing in how many passengers are in a train, in stations to be stopped at by displaying the training images or the like. The assisting apparatus 10 may display on the display section 160 various images such as an empty train where there is hardly any passenger, or a crowded train packed with passengers, depending on the physical state of the patient 200. The assisting apparatus 10 may extract an image of the patient 200 from a photograph in which the image of the patient 200 is captured, for combining the image of the patient 200 with training images. The assisting apparatus 10 may also show training images into which the image of the patient 200 has been incorporated to the patient 200. Note that the physical state of the patient 200 is identified by the image of the patient 200 captured by the image-capturing section 100, as well as the physical state of the patient 200 measured by the biological information measurement section 105. The physical state of the patient 200 may be information showing existence/nonexistence of blinks, the number of times of blinks per unit time, how the face looks down, change in the size of the pupils, existence/nonexistence of perspiration, change in blood pressure, etc., pertaining to the patient 200.

Furthermore, the assisting apparatus 10 may change the information quantity and the strength of a training image step by step depending on the physical state of a patient 200, and display on the display section 160 the training image of which the information quantity and the strength are changed. For example, the assisting apparatus 10 detects change of the physical state of the patient 200 looking at the display section 160 on real time basis. Then the assisting apparatus 10 displays on the display section 160 a training image by changing the strength thereof step by step. Accordingly, the assisting apparatus 10 is able to subject the patient 200 to a training image for phobia treatment, while preventing the patient 200 from having a panic attack. Note that the strength of a training image may be defined to be stronger as the resolution or tone of the training image gets higher. The strength of a training image may also be defined to be stronger as a certain image changes from the animation version to the photographed version step by step.

For example, the assisting apparatus 10 displays a predetermined training image on the display section 160 step by step, for a patient 200 suffering from a panic disorder attributed to agoraphobia. Concretely, as the first step, the assisting apparatus 10 shows a training image of an empty train to the patient 200 by displaying the same on the display section 160. Then the assisting apparatus 10 measures the physical state of the patient 200 on real time basis using the biological information measurement section 105. Next as the second step, the assisting apparatus 10 displays a training image of which the strength is increased step by step depending on the measurement result of biological information of the patient 200 measured by the biological information measurement section 105 on real time basis. For example, the assisting apparatus 10 displays on the display section 160 a training image in which the number of passengers in the train is increased step by step, for the patient 200 to look at. In this way, the assisting apparatus 10 is able to assist a patient 200 overcome his phobia, by changing the strength of a training image step by step depending on the physical state of a patient 200, and display the training image of which the strength is changed on the display section 160 to subject the patient 200 to the training image.

Figure 2:
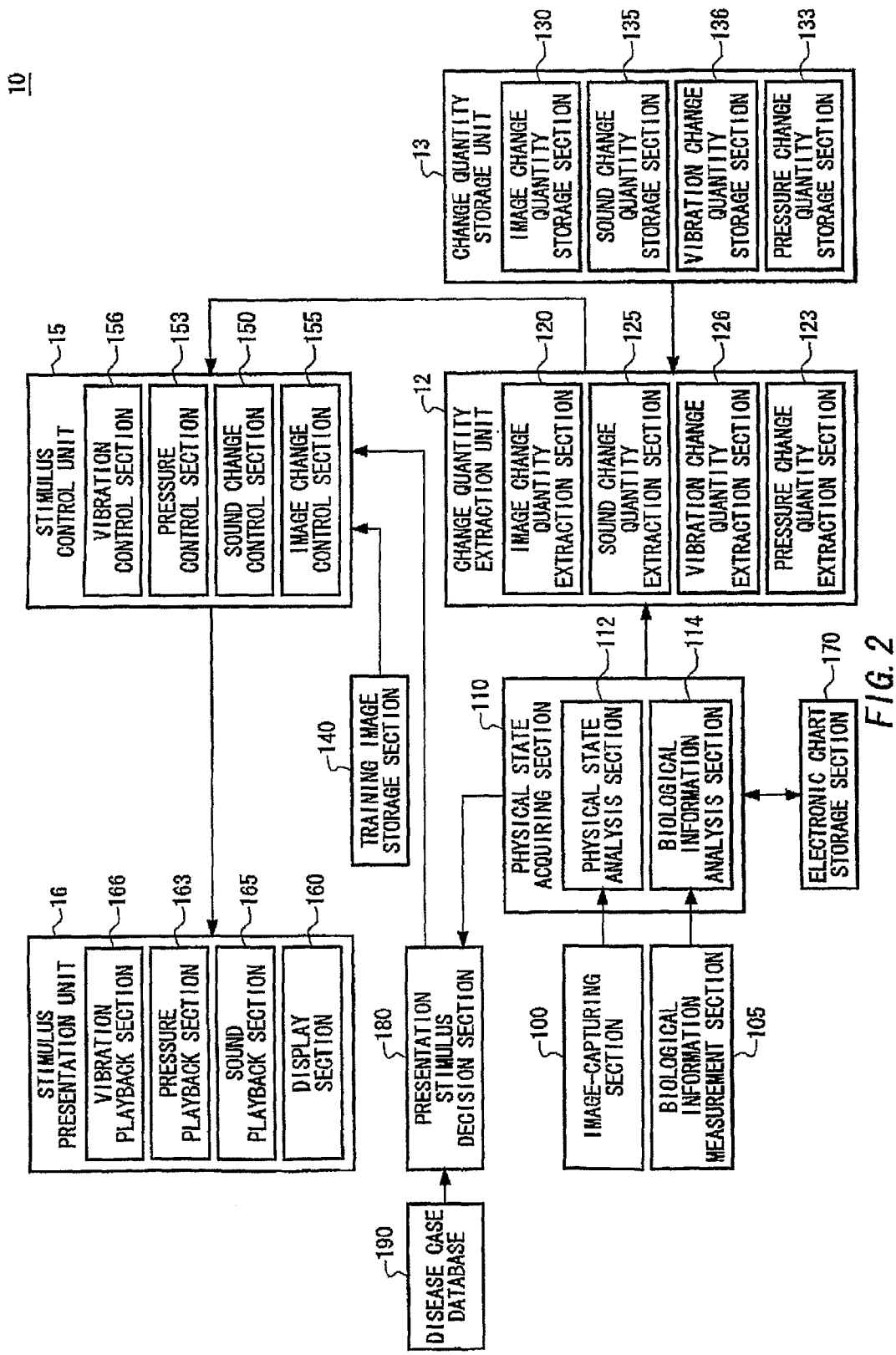
FIG. 2 is a block diagram showing a functional configuration of the mental illness treatment assisting apparatus 10.

FIG. 2 shows one example of a functional configuration of the assisting apparatus 10 according to the present embodiment. The assisting apparatus 10 includes an image-capturing section 100, a biological information measurement section 105, a physical state acquiring section 110, a change quantity extraction unit 12, a change quantity storage unit 13, a stimulus control unit 15, a stimulus presentation unit 16, a training image storage section 140, an electronic chart storage section 170, a presentation stimulus decision section 180, and a disease case database 190. Furthermore, the physical state acquiring section 110 includes a physical state analysis section 112 and a biological information analysis section 114. The change quantity extraction unit 12 includes an image change quantity extraction section 120, a sound change quantity extraction section 125, a vibration change quantity extraction section 126, and a pressure change quantity extraction section 123. Furthermore, the change quantity storage unit 13 includes an image change quantity storage section 130, a sound change quantity storage section 135, a vibration change quantity storage section 136, and a pressure change quantity storage section 133. Furthermore, the stimulus control unit 15 includes a sound change control section 150, an image change control section 155, a vibration control section 156, and a pressure control section 153. In addition, the stimulus presentation unit 16 includes a vibration playback section 166, a pressure playback section 163, a display section 160, and a sound playback section 165.

The training image storage section 140 stores a training image in association with a disease. Here, a training image may be an image representing a situation to which a patient 200 having a phobia such as panic syndrome feels fear or anxiety. A training image may be either a still image or a motion image. Furthermore, a training image may be a photographed version or an animation version. Furthermore, the training image storage section 140 may store a plurality of training images corresponding to the same scene but with different resolution. Specifically, the training image storage section 140 may store a plurality of training images differing in resolution from one another, such as a training image of high resolution considered as a level to which a patient 200 clearly feels fear or anxiety, a training image of low resolution considered as a level to which the patient 200 would not feel fear or anxiety so much as when the patient 200 looks at the training image of high resolution. For example, the training image storage section 140 may store, in association with a spider phobia, a training image of a photographed spider, a training image of a spider blurred in a predetermined blurring quantity, a training image of a schematic spider, and a training image of an animated spider, and so on.

Additionally, the training image storage section 140 may store a three-dimensional training image to which the patient 200 would feel stronger fear, and a two-dimensional training image to which the patient 200 would not feel fear so much as when the patient 200 looks at the three-dimensional training image.

Additionally, in storing three-dimensional images, the training image storage section 140 may store a plurality of training images that pop out in different degrees from each other.

The training image storage section 140 stores, in association with a training image for a predetermined phobia, sound of a situation represented by the training image. Specifically, the training image storage section 140 stores sound that the patient 200 feels when the patient 200 is placed in a situation indicated by the training image for a predetermined phobia. For example, when storing a training image of a crowded train in association with agoraphobia, the training image storage section 140 stores sound that can be heard in a crowded train, i.e. sound of the train running, conversation between passengers, and announcement by the conductor. The training image storage section 140 also stores sound heard in a train whose passenger ratio is low. The training image storage section 140 supplies a training image to the image change control section 155 according to control by the image change control section 155. Additionally, the training image storage section 140 supplies sound associated with the training image to the sound change control section 150 according to control by the sound change control section 150.

The training image storage section 140 may store sound that feels as if the sound source is moving by using a Doppler effect, a sound effect, a change in volume, or the like. Accordingly, it becomes possible to realize a situation that the patient 200 has trouble with a realistic sense. For example, in training a patient 200 having a phobia about bees, sound feeling as if a bee is approaching the patient 200 may be stored in association with a training image with higher strength. Further, the training image storage section 140 may store sound feeling as if a bee is resting in association with a training image with lower strength.

The training image storage section 140 stores, in association with a training image for a predetermined phobia, vibration corresponding to a situation that the training image represents. Specifically, the training image storage section 140 stores vibration felt by the patient 200 when the patient 200 is placed in the situation that the training image for the predetermined phobia represents. For example, the training image storage section 140 stores vibration of a train, in case of storing a training image of a crowded train in association with agoraphobia. The training image storage section 140 supplies vibration associated with a training image to the vibration control section 156 according to control by the vibration control section 156.

In addition, the training image storage section 140 stores, in association with a training image for a predetermined phobia, pressure of a situation that the training image represents. Specifically, the training image storage section 140 stores pressure felt by the patient 200 when the patient 200 is placed in the situation that the training image for the predetermined phobia represents. For example, in case of storing a training image of a crowded train in association with agoraphobia, the training image storage section 140 stores pressure that the patient 200 undergoes when pressed by surrounding passengers while on board the crowded train. The training image storage section 140 supplies pressure associated with a training image to the pressure control section 153 according to control by the pressure control section 153.

The display section 160 displays a training image according to control by the image change control section 155. Note that such display devices as a monitor and a stereoscopic television are examples of the display section 160. The sound playback section 165 plays back sound associated with a training image displayed by the display section 160, according to control by the sound change control section 150. The assisting apparatus 10 may include a plurality of sound playback sections 165. If the assisting apparatus 10 includes a plurality of sound playback sections 165 as stated above, it becomes possible to generate more realistic sense with which a training image is displayed by the display section 160 than in a case where there is only one sound playback section 165. Accordingly, when the sound playback section 165 plays back sound associated with a training image of agoraphobia, the patient 200 can feel a sense as if he is actually on board a train. Furthermore, the display section 160 may simultaneously display a plurality of training images.

The vibration playback section 166 plays back vibration associated with a training image displayed by the display section 160, according to control by the vibration control section 156, and gives the vibration to the patient 200. For example, the vibration playback section 166 may vibrate a supporting member 1660 supporting a patient 200, thereby giving the vibration to the patient 200. To be more specific, the supporting member 1660 may be a chair on which a patient 200 is invited to sit, and the chair may be vibrated. Alternatively, the supporting member 1660 may be a floor of a room used in diagnosis of a patient 200, and the room itself may be vibrated. For example, in case of displaying a training image of a crowded train associated with agoraphobia on the display section 160, the vibration playback section 166 subjects a patient 200 to vibration of a train associated with the training image. Accordingly, the patient 200 can feel as if he is actually on board such a train.

Furthermore, the pressure playback section 163 plays back pressure associated with a training image displayed by the display section 160, according to control by the pressure control section 153, and gives the vibration to the patient 200. The pressure playback section 163 may be a cloth in which a balloon is installed for a patient 200 to wear. Alternatively, the pressure playback section 163 may be a balloon installed in a room used in diagnosis of a patient 200. In either case, it becomes possible to play back a situation to which the patient 200 has a phobia about with a more realistic sense, by pumping up the balloon to press the patient 200. For example, in case of displaying a training image of a crowded train associated with agoraphobia on the display section 160, the pressure playback section 163 gives, to the patient 200, pressure incident in a crowded train associated with the training image. Accordingly, the patient 200 can feel as if he is actually on board such a train.

The image-capturing section 100 captures an image of the patient 200 looking at a training image displayed by the display section 160. The image-capturing section 100 captures an image of a patient 200 with resolution with which an expression of the patient 200 is identifiable, resolution with which the size of the pupils of the patient 200 is identifiable, and resolution with which the motion of the patient 200 is identifiable. Further, the assisting apparatus 10 may include a plurality of image-capturing sections 100. Furthermore, the image-capturing section 100 may be a three-dimensional camera, and an omnidirectional camera. The image-capturing section 100 supplies the image of the patient 200 having been captured, to the physical state analysis section 112 within the physical state acquiring section 110. The biological information measurement section 105 measures biological information of the patient 200. Biological information of a patient 200 may be information indicating heart rate, blood pressure, breathing quantity, temperature, change quantity thereof, existence/nonexistence of perspiration, change in perspiration, and so on. The biological information measurement section 105 supplies the measured biological information to the biological information analysis section 114 within the physical state acquiring section 110.

The physical state acquiring section 110 acquires a physical state of a patient 200 looking at a training image displayed by the display section 160. Specifically, the physical state acquiring section 110 acquires a motion of the patient 200 according to analysis performed by the physical state analysis section 112 within the physical state acquiring section 110 onto an image of the patient 200 having been captured by and received from the image-capturing section 100. For example, the physical state analysis section 112 detects a motion of the patient 200, from a plurality of images that the image-capturing section 100 has captured in a predetermined time interval. Subsequently, the physical state analysis section 112 judges whether the detected motion of the patient 200 corresponds to either of predetermined motions. Here, the predetermined motions may be change in expression of a patient 200 (e.g. from a smiling expression to without expression), existence/nonexistence of blinks, the number of times of blinks, the size of pupils, a motion of turning his eyes away, a motion of closing his eyes, a body lurch, a motion of turning his face away, a motion of looking down, a tremor, etc. The judgment about whether the patient 200 is actually turning his face away may be performed for example by extracting a skin color of an area corresponding to the face of a patient 200, and examining based on the change in area size of the extracted area corresponding to the face.

Specifically, the assisting apparatus 10 displays on the display section 160 an image not intended as a training image and to which the patient 200 does not feel fear or anxiety. For example, for a patient 200 having a phobia about spiders, an image that does not contain any spider is displayed, and the image-capturing section 100 captures an image of the patient 200 while he is not feeling fear or anxiety. Subsequently, the physical state analysis section 112 analyzes the image of the patient 200 captured by the image-capturing section 100, and detects a motion of the patient 200 when he is not feeling fear or anxiety. Meanwhile, the physical state analysis section 112 receives from the image-capturing section 100 an image in which a motion of the patient 200 is captured when a training image is displayed by the display section 160, and compares the received image with the image of the patient 200 while he is not feeling fear or anxiety. By using the comparison result, the physical state analysis section 112 acquires motions that he has taken in response to looking at the training image, from among the motions of the patient 200.

Further, the physical state analysis section 112 may acquire a change quantity per unit time of the motion of the patient 200, by analyzing an image of the patient 200 received from the image-capturing section 100. For example, the change quantity per unit time of the motion of the patient 200 may be the change quantity of the number of times of blinks per unit time of the patient 200, the change quantity per unit time of the size of the pupils, and the change quantity per unit time of the position of the line of sight, relating to the patient 200. Specifically, the physical state analysis section 112 receives an image of the patient 200 from the image-capturing section 100 for each predetermined time. The physical state analysis section 112 then analyzes each of a plurality of received images, and calculates the change quantity per unit time of the motion of the patient 200.

For example, the assisting apparatus 10 displays on the display section 160 an image not intended as a training image and to which the patient 200 would not feel fear or anxiety, for the patient 200 to look at. In this occasion, the physical state analysis section 112 analyzes an image received from the image-capturing section 100, and calculates the number of times of blinks per unit time of the patient 200. Next, the assisting apparatus 10 shows a training image to the patient 200. In this occasion, the physical state analysis section 112 analyzes the image received from the image-capturing section 100 for each predetermined time, and calculates the number of times per unit time of blinks of the patient 200 when the patient 200 feels fear or anxiety. Then the physical state analysis section 112 compares the number of times per unit time of blinks of the patient 200 when he is not feeling fear or anxiety with the number of times of blinks per unit time of the patient 200 when he is feeling fear or anxiety, and calculates the change quantity per unit time for the number of times of blinks of the patient 200. The physical state analysis section 112 supplies the acquired motion of the patient 200 and the change quantity per unit time for the motion of the patient 200, to the image change quantity extraction section 120 and the sound change quantity extraction section 125.

Then the biological information analysis section 114 within the physical state acquiring section 110 acquires the biological information of the patient 200 received from the biological information measurement section 105. For example, the assisting apparatus 10 first displays on the display section 160 an image not intended as a training image and to which the patient 200 would not feel fear or anxiety, for the patient 200 to look at. In this occasion, the biological information analysis section 114 acquires the biological information of the patient 200 received from the biological information measurement section 105, as biological information of the patient 200 when he is not feeling fear or anxiety. Next, the assisting apparatus 10 displays a training image on the display section 160. The biological information analysis section 114 compares the biological information of the patient 200 in this occasion with the biological information when the patient 200 is not feeling fear or anxiety, and acquires biological information having shown any change.

In addition, the biological information analysis section 114 acquires the change quantity per unit time of the biological information of the patient 200 measured by the biological information measurement section 105. For example, the assisting apparatus 10 first displays an image not intended as a training image and to which the patient 200 would not feel fear or anxiety, to the display section 160 for the patient 200 to look at. In this occasion, the biological information analysis section 114 analyzes the biological information of the patient 200 received from the biological information measurement section 105, and calculates biological information (e.g. heart rate) of the patient 200 per unit time. Next, the assisting apparatus 10 shows a training image to the patient 200. In this occasion, the biological information analysis section 114 analyzes the biological information of the patient 200 received from the biological information measurement section 105 for each predetermined time, and calculates the biological information per unit time of the patient 200 when the patient 200 is feeling fear or anxiety. Then the biological information analysis section 114 compares the biological information per unit time of the patient 200 when he is not feeling fear or anxiety with the biological information per unit time of the patient 200 when he is feeling fear or anxiety, and calculates the change quantity per unit time of the biological information of the patient 200. The biological information analysis section 114 supplies the acquired biological information of the patient 200 and the change quantity per unit time of the biological information of the patient 200, to the image change quantity extraction section 120 and the sound change quantity extraction section 125.

Further, the physical state acquiring section 110 supplies the motion of the patient 200 and the change quantity per unit time of the motion of the patient 200 acquired by the physical state analysis section 112, to the electronic chart storage section 170. Further, the physical state acquiring section 110 supplies the biological information of the patient 200 and the change quantity per unit time of the biological information of the patient 200 acquired by the biological information analysis section 114, to the electronic chart storage section 170. The electronic chart storage section 170 stores motion, biological information, etc. of the patient 200, in association with time. The electronic chart storage section 170 may supply a motion, biological information, etc. of the patient 200 in the past, to the physical state analysis section 112 and the biological information analysis section 114 according to control by the physical state acquiring section 110. For example, the physical state analysis section 112 may detect change in motion of the patient 200, by comparing the motion of the patient 200 in the past received from the electronic chart storage section 170 to the motion of the patient 200 obtained by analyzing an image received from the image-capturing section 100. Furthermore, the biological information analysis section 114 may compare the biological information of the patient 200 in the past received from the electronic chart storage section 170 and the biological information of the patient 200 received from the biological information measurement section 105, thereby detecting the change quantity of the biological information.

The image change quantity storage section 130 stores the change quantity of the information quantity of the training image displayed by the display section 160, in association with the physical state of the patient 200. Specifically, the image change quantity storage section 130 stores the change quantity of the information quantity of the training image displayed by the display section 160, in association with either the motion of the patient 200 being a physical state of the patient 200 or the change quantity per unit time of the motion of the patient 200. Additionally, the image change quantity storage section 130 may store the change quantity of the information quantity of the training image displayed by the display section 160, in association with either the biological information of the patient 200 being a physical state of the patient 200, or the change quantity per unit time of the biological information of the patient 200. Specifically, the change quantity of the information quantity of the training image stored in the image change quantity storage section 130 may be the change quantity of tone, resolution, contrast, dimension, the degree in which the three-dimensional image pops out, the field angle, and so on. Furthermore, the image change quantity storage section 130 may store the change quantity of the number of the training images simultaneously displayed by the display section 160, in association with the physical state of the patient 200.

The change in the information quantity of the training image stored in the image change quantity storage section 130 may be the change quantity of the image contents. For example, the change quantity of the image contents may be the change quantity caused in morphing from an image to which the patient 200 does not feel fear or anxiety (e.g. animation or a schematic diagram) to a training image to which the patient 200 feels fear or anxiety (e.g. a photographed version). The image change quantity storage section 130 supplies the change quantity of the information quantity of the training image to the image change quantity extraction section 120, according to control by the image change quantity extraction section 120. The sound change quantity storage section 135 stores the change quantity of the information quantity of sound played back by the sound playback section 165, in association with the physical state of the patient 200. For example, the change quantity of the information quantity of sound may be the change quantity of volume, the change quantity of the sound quality, or the like. The sound change quantity storage section 135 supplies the change quantity of the information quantity of sound to the sound change quantity extraction section 125. The vibration change quantity storage section 136 stores the change quantity of vibration given by the vibration playback section 166 to the patient 200, in association with a physical state of the patient 200. For example, the change quantity of vibration may be the change quantity of amplitude, phase, frequency, pattern, and the like, of the vibration. The vibration change quantity storage section 136 for vibration supplies the change quantity of vibration to the vibration change quantity extraction section 126. The pressure change quantity storage section 133 stores the change quantity of pressure given by the pressure playback section 163 to the patient 200, in association with a physical state of the patient 200. For example, the change quantity of pressure may be strength, direction, or the like of the pressure. The pressure change quantity storage section 133 supplies the change quantity of pressure to the pressure change quantity extraction section 123.

The image change quantity extraction section 120 extracts the change quantity of the information quantity of the training image that the image change quantity storage section 130 stores in association with the physical state of the patient 200 which has been obtained by the physical state acquiring section 110. Specifically, the image change quantity storage section 120 extracts the change quantity of the information quantity for the training image that the image change quantity storage section 130 stores in association with the motion of the patient 200 or the change quantity per unit time of the motion of the patient 200 acquired by the physical state analysis section 112. Additionally, the image change quantity extraction section 120 extracts the change quantity of the information quantity of the training image that the image change quantity storage section 130 stores in association with the biological information of the patient 200 or the change quantity per unit time of the biological information of the patient 200 acquired by the biological information analysis section 114. The image change quantity extraction section 120 supplies the change quantity of the information quantity of the extracted training image to the image change control section 155. The sound change quantity extraction section 125 extracts the change quantity of the information quantity of the sound that the sound change quantity storage section 135 stores in association with the physical state of the patient 200 acquired by the physical state acquiring section 110. The sound change quantity extraction section 125 supplies the extracted change quantity of the information of the sound, to the sound change control section 150. The vibration change quantity extraction section 126 extracts the change quantity of vibration that the vibration change quantity storage section 136 stores in association with the physical state of the patient 200 acquired by the physical state acquiring section 110. The vibration change quantity extraction section 126 supplies the extracted change quantity of the vibration to the vibration control section 156. The pressure change quantity extraction section 123 extracts the change quantity of pressure that the pressure change quantity storage section 133 stores in association with the physical state of the patient 200 acquired by the physical state acquiring section 110. The pressure change quantity extraction section 123 supplies the extracted change quantity of the pressure to the pressure control section 153.

According to the change quantity of the information quantity of the training image received from the image change quantity extraction section 120, the image change control section 155 changes the information quantity of the training image displayed by the display section 160. Specifically, the image change control section 155 changes tone, resolution, dimension, the degree in which the three-dimensional image pops out, the number of training images simultaneously displayed, contrast, and the like, relating to the training image(s) displayed by the display section 160. Additionally, the image change control section 155 may change the contents of the training image displayed by the display section 160. For example, the image change control section 155 displays a non-training image on the display section 160 when not receiving the change quantity of the information quantity of the training image from the image change quantity extraction section 120. Then after a predetermined time has elapsed, the image change control section 155 extracts and displays on the display section 160 a training image that the training image storage section 140 stores in association with a disease of a patient 200. In such cases, the image change control section 155 may display on the display section 160 a training image to which the patient 200 would feel fear or anxiety last from among the training images to which the patient 200 would feel fear or anxiety. A training image to which the patient 200 would feel fear or anxiety last is for example an image of inside a train where there is no passenger, which represents a situation where there is no sound of train running or train announcement, as a training image for agoraphobia.

In receiving the change quantity of the information quantity of a training image from the image change quantity extraction section 120, the image change control section 155 changes the training image according to the received change quantity of the information quantity. For example, suppose a case where the biological information measurement section 105 is measuring the change quantity of a heart rate per unit time as a physical state of the patient 200. In such a case, the biological information measurement section 105 first measures a heart rate per unit time for a patient 200 when a non-training image is displayed by the display section 160. Next, after a predetermined time has elapsed, the image change control section 155 displays a training image to which the patient 200 would feel fear or anxiety last on the display section 160. Then the biological information measurement section 105 measures a heart rate per unit time of a patient 200 in this occasion. The biological information analysis section 114 compares the heart rate per unit time of the patient 200 when he is looking at the non-training image and the heart rate per unit time of the patient 200 when he is looking at the training image, and calculates the change quantity of the heart rate per unit time.

Then the image change quantity extraction section 120 extracts the change quantity of the information quantity of a training image that the image change quantity storage section 130 stores in association with the change quantity of a heart rate per unit time calculated by the biological information analysis section 114, and supplies the same to the image change control section 155. For example, the image change quantity storage section 130 may store a larger change quantity as the change quantity of the information quantity of the training image toward a negative direction, in association with a case where the change quantity toward a positive direction of a heart rate per unit time is larger. In addition, the image change quantity storage section 130 may store a larger change quantity as the change quantity toward a positive direction of the information quantity of a training image, in association with a case where the change quantity of a heart rate per unit time toward a negative direction is larger. The image change control section 155 changes the training image stored in the training image storage section 140, according to the change quantity of the information quantity of the training image received from the image change quantity extraction section 120. The image change control section 155 controls the display section 160 to display the training image of which the information quantity has been changed. The sound change control section 150 changes the information quantity of sound played back by the sound playback section 165 according to the change quantity of sound information received from the sound change quantity extraction section 125. The sound change control section 150 controls the sound playback section 165 to play back the sound of which the information quantity has been changed.

Next, the image change control section 155 controls the display section 160 to display the training image of which the information quantity has been changed step by step. Specifically, the image change control section 155 displays the training image of which the strength has been changed to the display section 160, according to the change quantity extracted by the image change quantity extraction section 120 in accordance with the result of the physical state analysis section 112 and the biological information analysis section 114 measuring the physical state of the patient 200 on real time basis. Likewise, the sound change control section 150 controls the sound playback section 165 to play back the sound of which the information quantity has been changed, according to the change quantity extracted by the sound change quantity extraction section 125. The vibration control section 156 controls the vibration playback section 166 to play back the vibration changed according to the change quantity extracted by the vibration change quantity extraction section 126. Furthermore, the pressure control section 153 controls the pressure playback section 163 to play back the pressure having been changed according to the change quantity extracted by the pressure change quantity extraction section 123.

Here, when the change quantity of the physical state of the patient 200 per unit time and within a predetermined time lies within a predetermined range, the image change control section 155 may sequentially display the training image of which the strength has been increased step by step on the display section 160. On the contrary, when the change quantity of the physical state of the patient 200 per unit time and within a predetermined time exceeds the predetermined range, the image change control section 155 displays the training image of which the strength has been decreased on the display section 160. Likewise, the sound change control section 150 controls the sound playback section 165 to play back the sound of which the information quantity has been changed, in accordance with the change quantity per unit time of the physical state of the patient 200. Furthermore, the vibration control section 156 controls the vibration playback section 166 to play back the vibration changed in accordance with the change quantity per unit time of the physical state of the patient 200. Furthermore, the pressure control section 153 controls the pressure playback section 163 to play back the pressure changed in accordance with the change quantity per unit time of the physical state of the patient 200.

The assisting apparatus 10 according to the present embodiment detects the physical state of the patient 200 on real time basis thereby enabling display of the training image of which the information quantity, the strength, and the contents are changed in accordance with the physical state as well as the change in physical state of the patient 200. Accordingly, the assisting apparatus 10 according to the present embodiment is able to automatically display a training image suited for treating the phobia of the patient 200 by restraining the occurrence of the patient 200 having an attack such as a panic attack.

FIG. 3 shows one example of a data structure of the image change quantity storage section 130 according to the present embodiment. The image change quantity storage section 130 stores the change quantity of the information quantity of the training image in association with the physical state of the patient 200. Specifically, the image change quantity storage section 130 stores the change quantity of the information quantity of the training image in association with the change in expression of the patient 200 and the motion of the patient 200. For example, the image change quantity storage section 130 stores the change quantity of the information quantity of the training image, in association with the motion of closing the eyes, the motion of turning the eyes away, the expression such as a smiling face, and the motion of the patient 200 lurching, the motion of the patient 200 looking down, the motion of the patient 200 shaking his head, respectively being the motion of the patient 200. For example, the image change quantity storage section 130 may store the change quantity of reducing the tone, resolution, or contrast of the training image, in association with the motion by which the patient 200 is judged to be feeling fear or anxiety.

For example, when the patient 200 has closed his eyes, the image change control section 155 receives the change quantity of the information quantity of the training image associated with the motion of the patient 200 closing his eyes, which the image change quantity extraction section 120 has extracted from the image change quantity storage section 130. Then the image change control section 155 changes the training image according to the received change quantity. For example, when the patient 200 has closed his eyes, the image change control section 155 receives the change quantity that indicates to decrease the tone of the training image by 4 bits. Then the image change control section 155 controls the display section 160 to display the training image by decreasing the tone thereof by 4 bits, based on the received quantity. Accordingly, when the patient 200 feels fear, the training image can be changed to a version of which the tone has been lowered, thereby enabling to display a training image automatically salving the fear of the patient 200. Likewise, the image change control section 155 is able to change the information quantity of the training image for example by increasing the tone of the training image by 6 bits when the patient 200 is smiling, or by decreasing the tone of the training image by 2 bits when the patient 200 has looked down.

FIG. 4 shows one example of a data structure of the image change quantity storage section 130 according to the present embodiment. The image change quantity storage section 130 stores the change quantity of the information quantity of the training image in association with the biological information of the patient 200 as the physical state. For example, the image change quantity storage section 130 may store change quantities respectively of tone, resolution, contrast, and the like, in association with information indicating perspiration/non-perspiration on the patient 200, information showing that the blood pressure of the patient 200 has exceeded a predetermined value or the like as the biological information of the patient 200 respectively. Specifically, the image change quantity storage section 130 may store the change quantity used in decreasing the tone, resolution, or contrast of the training image, in association with the biological information that the patient 200 shows when he is feeling fear or anxiety. For example, the image change quantity storage section 130 may store the change quantity indicating to decrease the tone of a training image by 4 bits in association with a case where the patient 200 has caused perspiration. On the other hand, the image change quantity storage section 130 may store the change quantity indicating to increase the tone of the training image by 6 bits in association with a case where the patient 200 does not causes any perspiration.

FIG. 5 shows one example of a data structure of the image change quantity storage section 130 according to the present embodiment. The image change quantity storage section 130 stores, as physical state, the change quantity of the information quantity of a training image, in association with the change quantity per unit time of the biological information of the patient 200. For example, the image change quantity storage section 130 may store the change quantity of further lowering the tone, resolution, or contrast, in association with the change quantity of the number of times of blinks per unit time calculated by the physical state analysis section 112, as the change quantity of the number of times of blinks per unit time gets larger, by comparing the number of times of blinks per unit time when the patient 200 is not looking at a training image and the number of times of blinks per unit time when the patient 200 is looking at a training image. On the other hand, the image change quantity storage section 130 may store the change quantity of further raising the tone, resolution, or contrast, in association with a case where the change quantity of the number of times of blinks per unit time becomes smaller or further reduced. For example, the image change quantity storage section 130 may store the change quantity indicating to decrease the tone of the training image by 4 bits, in association with a case where the change quantity of the number of times of blinks per unit time of the patient 200 is increased by 50 times. On the other hand, the image change quantity storage section 130 may store the change quantity indicating to increase the tone of the training image by 6 bits in association with a case where the number of times of blinks per unit time of the patient 200 is decreased by 30 times.

The presentation stimulus decision section 180 decides a method for presenting a plurality of kinds of stimulus such as image, sound, vibration, and pressure to the patient 200. For example, the presentation stimulus decision section 180 may decide a method of presenting a plurality of kinds of stimulus, based on the physical state of the patient 200 detected by the physical state acquiring section in case of changing the strength of the training image, and the physical state of the patient 200 detected by the physical state acquiring section in case of changing the strength of the stimulus by means of the sound. For example, the presentation stimulus decision section 180 may control the image change control section 155 and the sound change control section 150 so that the stimulus yielding a larger change quantity in the physical state is presented to the patient 200 as a result of comparison between the change quantity of the physical state of the patient 200 detected by the physical state acquiring section when the strength of the training image is changed, and the change quantity of the physical state of the patient 200 detected by the physical state acquiring section when the strength of the stimulus by means of the sound is changed.

In addition, the presentation stimulus decision section 180 may adjust the ratio of the strength of the training image and the strength of the stimulus by means of the sound, according to the change quantity of the physical state of the patient 200 detected by the physical state acquiring section in the case of changing the strength of the training image and the change quantity of the physical state of the patient 200 detected by the physical state acquiring section in the case of changing the strength of the stimulus by means of the sound.

The disease case database 190 stores a method of presenting a plurality of kinds of stimulus in association with disease cases of mental illnesses. The presentation stimulus decision section 180 may present a plurality of kinds of stimulus to the patient 200, based on the method of presenting stimulus extracted from the disease case database 190. For example, the disease case database 190 may store, in association with agoraphobia, a combination of a visual stimulus by means of the training image of a crowded train displayed by the display section 160, and the sound stimulus by means of the sound of a train played back by the sound payback section 165, stimulus by means of vibration of a train given by the vibration playback section 166 to the patient 200, and stimulus by means of pressure of a crowded train given by the pressure playback section 163 to the patient 200. Additionally, the disease case database 190 may store the strength used in presenting these stimuli in association with each stimulus. In this occasion, the presentation stimulus decision section 180 may extract a method of presenting stimulus suited for the case of the mental illness of the patient 200, from the disease case database 190.

Figure 6:
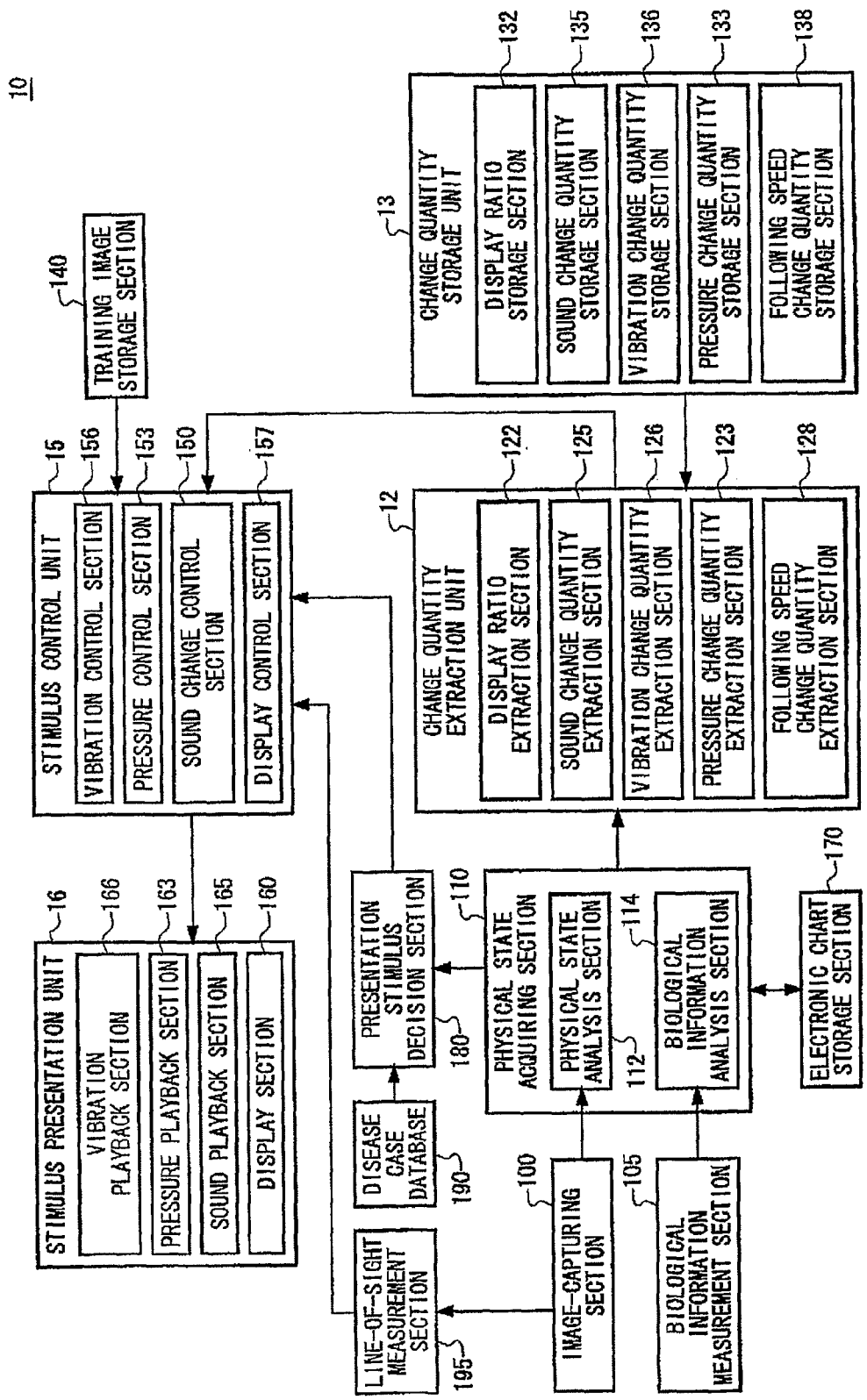
FIG. 6 is a block diagram showing a functional configuration of the mental illness treatment assisting apparatus 10.

FIG. 6 shows an example of a functional configuration of the assisting apparatus 10 according to other embodiments of the present invention. The assisting apparatus 10 includes: an image-capturing section 100; a biological information measurement section 105, a physical state acquiring section 110, a change quantity extraction unit 12, a change quantity storage unit 13, a stimulus control unit 15, a stimulus presentation unit 16, a training image storage section 140, an electronic chart storage section 170, a presentation stimulus decision section 180, a disease case database 190, and a patient's line-of-sight measurement section 195. Further, the physical state acquiring section 110 includes a physical state analysis section 112 and a biological information analysis section 114. In addition, the change quantity extraction unit 12 includes a display ratio extraction section 122, a sound change quantity extraction section 125, a vibration change quantity extraction section 126, a pressure change quantity extraction section 123, and a following speed change quantity extraction section 128. Further, the change quantity storage unit 13 includes a display ratio storage section 132, a sound change quantity storage section 135, a vibration change quantity storage section 136, a pressure change quantity storage section 133, and a following speed change quantity storage section 138. Further, the stimulus control unit 15 includes a sound change control section 150, a display control section 157, a vibration control section 156, and a pressure control section 153. The stimulus presentation unit 16 includes a vibration playback section 166, a pressure playback section 163, a display section 160, and a sound playback section 165. Note that the assisting apparatus 10 according to the present embodiment may be further equipped with part or all of the configuration or function of the assisting apparatus 10 described with use of the drawings from FIG. 1 to FIG. 5. Also, the members named the same as the members explained pertaining to the drawings from FIG. 1 to FIG. 5 have substantially the same functions, and so are not described in detail. First, the training image storage section 140 stores a training image in association with a disease. Further, the training image storage section 140 stores, in association with a training image for a predetermined phobia, sound of a situation represented by the training image. The training image storage section 140 supplies a training image to the display control section 157 according to control by the display control section 157. Furthermore, the training image storage section 140 supplies sound associated with the training image to the sound change control section 150, according to control by the sound change control section 150. Note that non-training images may be images from a television program, a movie, or the like.

The display section 160 displays a training image according to control by the display control section 157. The display section 160 may display a training image by inserting the training image to non-training images, according to control by the display control section 157. For example, the display section 160 displays a training image by inserting the training image into a plurality of motion picture element images constituting a motion picture, according to control by the display control section 157. Here, the motion picture element images may include frame images, field images, and any other images in various formats constituting a motion picture. Additionally, the display section 160 may display a non-training image and a training image by combining them, or display a non-training image and a training image by superimposing one on the other. Here, "combining a non-training image and a training image" may mean to dispose each of a non-training image and a training image in a respective predetermined area within the same display area of the display section 160, to present them as one screen of image. Furthermore, "superimposing a non-training image and a training image" may mean to superimpose, for display, a non-training image and a training image in the same display area of the display section 160. When the display section 160 displays a result of superimposing a non-training image with a training image, the training image may be rendered half-transparent in advance.

Further, the display section 160 may display a training image and a non-training image at a predetermined quantitative ratio. Further, the display section 160 may display a training image and a non-training image in respectively different dimensions.

The sound playback section 165 plays back sound associated with a training image displayed by the display section 160, according to control by the sound change control section 150. The image-capturing section 100 captures an image of a patient 200 looking at the training image displayed by the display section 160. The image-capturing section 100 supplies the captured image of the patient 200 to the physical state analysis section 112 within the physical state acquiring section 110. The biological information measurement section 105 measures biological information of the patient 200 looking at the training image displayed by the display section 160. The biological information measurement section 105 supplies the measured biological information to the biological information analysis section 114 within the physical state acquiring section 110. The physical state acquiring section 110 acquires a physical state of the patient 200 looking at the training image displayed by the display section 160. Specifically, the physical state analysis section 112 within the physical state acquiring section 110 acquires the motion of the patient 200 by analyzing the image of the patient 200 received from the image-capturing section 100. Further, the physical state analyzing section 112 may acquire the change quantity per unit time of the motion of the patient 200, by analyzing the image of the patient 200 received from the image-capturing section 100. The physical state analysis section 112 supplies the acquired motion of the patient 200 as well as change quantity per unit time of the motion of the patient 200, to the display ratio extraction section 122 and the sound change quantity extraction section 125.

Furthermore, the biological information analysis section 114 within the physical state acquiring section 110 acquires the biological information of the patient 200 received from the biological information measurement section 105. In addition, the biological information analysis section 114 acquires the change quantity per unit time of the biological information of the patient 200 measured by the biological information measurement section 105. The biological information analysis section 114 supplies the acquired biological information of the patient 200 and the change quantity per unit time of the biological information of the patient 200, to the display ratio extraction section 122 and the sound change quantity extraction section 125. Further, the physical state acquiring section 110 supplies the motion of the patient 200 and the change quantity per unit time of the motion of the patient 200 acquired by the physical state analysis section 112, to the electronic chart storage section 170. Further, the physical state acquiring section 110 supplies the biological information of the patient 200 and the change quantity per unit time of the biological information of the patient 200 acquired by the biological information analysis section 114, to the electronic chart storage section 170. The electronic chart storage section 170 stores a motion, biological information, etc. of the patient 200 in association with time. The electronic chart storage section 170 may supply a motion, biological information, etc. of the patient 200 in the past, to the physical state analysis section 112 and the biological information analysis section 114 according to control by the physical state acquiring section 110.

The display ratio storage section 132 stores, in association with the physical state of the patient 200, the change quantity of the display ratio of the training image displayed by the display section 160. Specifically, the display ratio storage section 132 stores, in association with the physical state of the patient 200, the change quantity of the display time of the training image displayed by the display section 160. Here, the unit used in expressing the change quantity of the display time may be minute, second, and microsecond. Additionally, the display ratio storage section 132 may store, in association with the physical state of the patient 200, the change quantity of the combination ratio of the training image displayed by the display section 160, or the change quantity of the degree of superimposing thereof. Further, the display ratio storage section 132 may store the change quantity of the display ratio of the training image displayed by the display section 160, in association with the motion of the patient 200 or the change quantity per unit time of the motion of the patient 200, being the physical state of the patient 200.

Additionally, in case of displaying a training image and a non-training image on the display section 160 at a predetermined quantitative ratio, the display ratio storage section 132 may store the change quantity of the quantitative ratio. Further, in case of displaying a training image and a non-training image on the display section 160 in respectively different dimensions, the display ratio storage section 132 may store the dimension of the training image and the dimension of the non-training image.

The display ratio storage section 132 may store the change quantity of the training image displayed by the display section 160, in association with the biological information of the patient 200 or the change quantity per unit time of the biological information of the patient 200, being the physical state of the patient 200. When the change quantity of the physical state of the patient 200 in a predetermined time falls within a predetermined range, the display ratio storage section 132 may store the change quantity employed in either increasing or decreasing the display ratio step by step. Further, the display ratio storage section 132 may store the change quantity of the degree of half-transparency of the training image, in association with the physical state of the patient 200. The display ratio storage section 132 supplies the change quantity of the display ratio of the training image to the display ratio extraction section 122, according to control by the display ratio extraction section 122. The sound change quantity storage section 135 stores the change quantity of the information quantity of the sound played back by the sound payback section 165, in association with the physical state of the patient 200. The sound change quantity storage section 135 supplies the change quantity of the information quantity of the sound to the sound change quantity extraction section 125. The vibration change quantity storage section 136 stores the change quantity of the vibration given by the vibration playback section 166 to the patient 200, in association with the physical state of the patient 200. The vibration change quantity storage section 136 supplies the change quantity of the vibration to the vibration change quantity extraction section 126. The pressure change quantity storage section 133 stores the change quantity of the pressure given by the pressure playback section 163 to the patient 200, in association with the physical state of the patient 200. The pressure change quantity storage section 133 supplies the change quantity of the pressure to the pressure change quantity extraction section 123.

The display ratio extraction section 122 extracts the change quantity of the display ratio of the training image that the display ratio storage section 132 stores in association with the physical state of the patient 200 acquired by the physical state acquiring section 110. Specifically, the display ratio extraction section 122 extracts the change quantity of the display time of the training image that the display ratio storage section 132 stores in association with the physical state of the patient 200 acquired by the physical state analysis section 112 within the physical state acquiring section 110. Further, the display ratio extraction section 122 extracts the change quantity of the combination ratio of the training image or the change quantity of the degree of superimposing thereof that the display ratio storage section 132 stores in association with the physical state of the patient 200 acquired by the physical state analysis section 112.

Further, the display ration extraction section 122 extracts the change quantity of the display ratio of the training image that the display ratio storage section 132 stores in association with the motion of the patient 200 or the change quantity per unit time of the motion of the patient 200 acquired by the physical state analysis section 112. The display ratio extraction section 122 may extract the change quantity of the display time of the training image that the display ratio storage section 132 stores in association with the biological information of the patient 200 or the change quantity per unit time of the biological information of the patient 200 acquired by the physical state analysis section 112. The sound change quantity extraction section 125 extracts the change quantity of the information quantity of the sound that the sound change quantity storage section 135 stores in association with the physical state of the patient 200 acquired by the physical state acquiring section 110. The sound change quantity extraction section 125 supplies the extracted change quantity of the information of the sound to the sound change control section 150.

Further, the display ratio extraction section 122 may extract the change quantity of a quantitative ratio in case of displaying a training image and a non-training image at a predetermined quantitative ratio on the display section 160 that the display ratio storage section 132 stores in association with the physical state of the patient 200 acquired by the physical state analysis section 112. Additionally, the display ratio extraction section 122 may extract dimensions of a training image and a non-training image in case of displaying the training image and the non-training image in respectively different dimensions on the display section 160 that the display ratio storage section 132 stores in association with the physical state of the patient 200 acquired by the physical state analysis section 112.

The display control section 157 changes the display ratio of the training image displayed by the display section 160 in accordance with the display ratio of the training image extracted by the display ratio extraction section 122. Specifically, the display control section 157 changes the display time of the training image displayed by the display section 160 in accordance with the change quantity of the display time of the training image extracted by the display ratio extraction section 122. For example, the physical state of the patient 200 indicates that he is not feeling fear or anxiety (e.g. when the patient 200 is smiling), the display ratio storage section 132 stores, in association with a smiling face, the change quantity of the display time indicating to display the training image longer compared to a case when the physical state of the patient 200 indicates that he is feeling fear or anxiety. Moreover, when the patient 200 is smiling, the display ratio extraction section 122 extracts the change quantity of the display time that the display ratio storage section 132 stores in association with a smiling face, and supplies the same to the display control section 157. The display control section 157 displays the display time of the training image by lengthening it to the display section 160, according to the change quantity of the display time received from the display ratio extraction section 122.

For example, the display control section 157 controls the display section 160 to display a non-training image, in case of not having received a display ratio of the training image from the display ratio extraction section 122. Then after elapse of a predetermined time, the display control section 157 extracts a training image that the training image storage section 140 stores in association with the disease of the patient 200, and causes the display section 160 to display the extracted training image. In such a case, the display control section 157 may control the display section 160 to display a training image to which the patient 200 would feel fear or anxiety the last from among the training images to which the patient 200 would feel fear or anxiety. A training image to which the patient 200 would feel fear or anxiety last is for example an image of an animated spider of a size smaller than a predetermined size with respect to the display area of the display section 160, in case of a training image for a phobia about spiders.

When receiving the change quantity of the display ratio of the training image from the display ratio extraction section 122, the display control section 157 changes the display ratio of the training image in accordance with the received change quantity of the display ratio. For example, suppose a case where the biological information measurement section 105 is measuring the change quantity of the heart rate per unit time as the physical state of the patient 200. In such a case, the biological information measurement section 105 first measures the heart rate per unit time of the patient 200 when a non-training image is on display on the display section 160. After elapse of a predetermined time, the display control section 157 controls the display section 160 to display a training image to which the patient 200 would feel fear or anxiety last. Then the biological information measurement section 105 measures the heart rate per unit time of the patient 200 in this occasion. The biological information analysis section 114 calculates the change quantity of the heart rate per unit time, by comparing the heart rate per unit time of the patient 200 when he is looking at a non-training image and the heart rate per unit time of the patient 200 when he is looking at a training image.

The display ratio extraction section 122 extracts the change quantity of the display ratio of the training image that the display ratio storage section 132 stores in association with the change quantity of the heart rate per unit time calculated by the biological information analysis section 114, and supplies the same to the display control section 157. For example, the display ratio storage section 132 may store a larger change quantity as the change quantity of the display ratio of the training image toward the negative direction, in association with a case where the change quantity of the heart rate per unit time toward a positive direction is larger. In addition, the display ratio storage section 132 may store a larger change quantity as the change quantity of the display ratio of the training image toward the positive direction, in association with a case where the change quantity of the heart rate per unit time toward a negative direction is larger. The display control section 157 changes the display ratio of the training image stored by the training image storage section 140, in accordance with the change quantity of the display ratio of the training image received from the display ratio extraction section 122. Then the display control section 157 controls the display section 160 to display the training image of which the display ratio has been changed.

Also, the display control section 157 changes the combination ratio or the superimposing degree of the training image displayed by the display section 160, in accordance with the change quantity of the combination ratio or the change quantity of the superimposing degree of the training image extracted by the display ratio extraction section 122. For example, the display ratio storage section 132 may store a larger change quantity as the combination ratio or the superimposing degree of the training image toward a negative direction, in association with a case where the change quantity per unit time of the heart rate towards a positive direction is larger. Further, the display ratio storage section 132 may store a larger change quantity as the combination ratio or the superimposing degree of the training image toward a positive direction, in association with a case where the change quantity per unit time of the heart rate toward a negative direction is larger. The sound change control section 150 changes the information quantity of the sound played back by the sound playback section 165, in accordance with the change quantity of the sound information received from the sound change quantity extraction section 125. The sound change control section 150 controls the sound playback section 165 to play back the sound of which the information quantity has been changed.

Further, the display control section 157 changes the number of the training images simultaneously displayed by the display section 160, in accordance with the change quantity of the number of the simultaneously displayed training images extracted by the display ratio extraction section 122. For example, the display ratio storage section 132 may store a larger change quantity as the change quantity of the number of the simultaneously displayed training images toward a negative direction, in association with a case where the change quantity per unit time of the heart rate toward a positive direction is larger. In addition, the display ratio storage section 132 may store a larger change quantity as the change quantity of the number of the simultaneously displayed training images toward a positive direction, in association with a case where the change quantity per unit time of the heart rate toward a negative direction is larger.

In addition, the display control section 157 changes the dimension of the training image displayed by the display section 160, in accordance with the change quantity of the dimension of the training image extracted by the display ratio extraction section 122. For example, the display ratio storage section 132 may store a larger change quantity as the change quantity of the dimension of the training image toward a negative direction, in association with a case where the change quantity per unit time of the heart rate toward a positive direction is larger. In addition, the display ratio storage section 132 may store a larger change quantity as the change quantity of the dimension of the training image toward a positive direction, in association with a case where the change quantity per unit time of the heart rate toward a negative direction is larger.

In addition, the display control section 157 changes the degree in which the training image displayed by the display section 160 pops out, in accordance with the change quantity of the degree in which the training image pops out when displaying a three-dimensional training image extracted by the display ratio extraction section 122. For example, the display ratio storage section 132 may store a larger change quantity as the change quantity of the degree in which the training image pops out toward a negative direction, in association with a case where the change quantity per unit time of the heart rate toward a positive direction is larger. Further, the display ratio storage section 132 may store a larger change quantity, as the change quantity of the degree in which the training image pops out in a positive direction, in association with a case where the change quantity per unit time of the heart rate toward a negative direction is larger.

The patient's line-of-sight measurement section 195 detects the direction of the line of sight of the patient 200, from the image of the patient 200 captured by the image-capturing apparatus 100. The display control section 157 may display the training image in a position of the display section 160 that is positioned in the direction of the line of sight detected by the patient's line-of-sight measurement section 195. In addition, the display control section 157 may control the display position of the training image to follow the direction of the line of sight of the patient 200.

The following speed change quantity storage section 138 stores the change quantity of the speed in which the training image displayed by the display section 160 is caused to follow the direction of the line of sight of the patient 200, in association with the physical state of the patient 200. Additionally, the following speed change quantity storage section 138 may store the speed in which the training image displayed by the display section 160 is caused to follow the direction of the line of sight of the patient 200, in association with the motion of the patient 200 or the change quantity per unit time of the motion of the patient 200 being the physical state of the patient 200. Further, the following speed change quantity storage section 138 may store information indicating to coercively set the display following speed to 0 (zero, stop without following) in association with a physical state indicating that the patient 200 is under excessive stress. Some examples of the physical state indicating that the patient 200 is under excessive stress is that he continues closing his eyes for more than a predetermined time, that the change quantity of his heart rate exceeds a predetermined value, etc.

Then the following speed change quantity storage section 138 may store the change quantity of the speed in which the training image displayed by the display section 160 is caused to follow the direction of the line of sight of the patient 200, in association with the change quantity per unit time of the biological information of the patient 200 or the change quantity per unit time of the biological information of the patient 200, being the physical state of the patient 200. The following speed change quantity storage section 138 may store the change quantity used in increasing or decreasing the speed of following, when the change quantity of the physical state of the patient 200 within a predetermined time falls within a predetermined range. The following speed change quantity storage section 138 supplies the change quantity of the speed in which the training image is caused to follow the line of sight of the patient 200, to the following speed change quantity extraction section 128 according to control by the following speed change quantity extraction section 128.

The following speed change quantity extraction section 128 extracts the change quantity of the speed of causing the training image to follow the direction of the line of sight of the patient 200, which is stored in the following speed change quantity storage section 138 in association with the physical state of the patient 200 acquired by the physical state acquiring section 110. Specifically, the following speed change quantity extraction section 128 extracts the change quantity of the speed of causing the training image to follow the direction of the line of sight of the patient 200, which is stored in the following speed change quantity storage section 138 in association with the physical state of the patient 200 acquired by the physical state analysis section 112 within the physical state acquiring section 110.

Further, the following speed change quantity extraction section 128 extracts the change quantity of the speed of causing the training image to follow the direction of the line of sight of the patient 200, which is stored in the following speed change quantity storage section 138 in association with the motion of the patient 200 or the change quantity per unit time of the motion of the patient 200 acquired by the physical state analysis section 112. Then the following speed change quantity extraction section 128 may extract the change quantity of the speed of causing the training image to follow the direction of the line of sight of the patient 200, which is stored in the following speed change quantity storage section 138 in association with the biological information of the patient 200 or the change quantity per unit time of the biological information of the patient 200 acquired by the physical state analysis section 112.

The display control section 157 changes the speed of causing the training image displayed by the display section 160 to follow the direction of the line of sight of the patient 200, in accordance with the speed of causing the training image extracted by the following speed change quantity extraction section 128 to follow the direction of the line of sight of the patient 200. For example, when the physical state of the patient 200 indicates that he is not feeling fear or anxiety (e.g. when the patient 200 is smiling), the following speed change quantity storage section 138 stores, in association with a smiling face, the change quantity of the speed so that the training image is caused to follow the direction of the line of sight of the patient 200 faster than in the case where the physical state of the patient 200 indicates that he is feeling fear or anxiety. When the patient 200 is smiling, the following speed change quantity extraction section 128 extracts the change quantity of the speed of causing the training image to follow the direction of the line of sight of the patient 200 which is stored in the following speed change quantity storage section 138 in association with a smiling face, and supplies the extracted change quantity to the display control section 157. The display control section 157 displays the speed of causing the training image to follow the direction of the line of sight of the patient 200 to the display section 160 after increasing the speed in accordance with the change quantity of the speed received from the following speed change quantity extraction section 128.

For example, when not having received the speed of causing the training image to follow the direction of line of sight of the patient 200 from the following speed change quantity extraction section 128, the display control section 157 controls the display section 160 to display the training image without moving the training image. In this occasion, the display control section 157 may display the training image at a predetermined position in the display section 160, or display the training image in a position corresponding to the direction of the line of sight of the patient 200 in the initial stage of displaying the training image. Then after elapse of a predetermined time, the display control section 157 controls the display section 160 to display the training image while causing the training image to follow the direction of the line of sight of the patient 200 at a predetermined speed.

When having received the change quantity of the speed of causing the training image to follow the direction of the line of sight of the patient 200 from the following speed change quantity extraction section 128, the display control section 157 changes the speed of causing the training image to follow the direction of the line of sight of the patient 200 in accordance with the received change quantity of the speed. For example, suppose a case where the biological information measurement section 105 is measuring the change quantity of the heart rate per unit time as the physical state of the patient 200. In such a case, the biological information measurement section 105 first measures the heart rate per unit time of the patient 200 while the training image is displayed by the display section 160 without being moved. Next, after a predetermined time has elapsed, the display control section 157 displays the training image on the display section 160 by causing the training image to follow the direction of the line of sight of the patient 200 at a predetermined speed. Then the biological information measurement section 105 measures the heart rate per unit time of the patient 200 in this occasion. The biological information analysis section 114 compares the heart rate per unit time of the patient 200 when he is looking at a training image not moving and the heart rate per unit time of the patient 200 when he is looking at a training image that is caused to follow the direction of the line of sight, and calculates the change quantity of the heart rate per unit time.

Then the following speed change quantity extraction section 128 extracts the change quantity of the speed of causing the training image to follow the direction of the line of sight of the patient 200 which is stored in the following speed change quantity storage section 138 in association with the change quantity of the heart rate per unit time calculated by the biological information analysis section 114, and supplies the same to the display control section 157. For example, the following speed change quantity storage section 138 may store a larger change quantity as the change quantity toward a negative direction of the speed of causing the training image to follow the direction of the line of sight, in association with a case where the change quantity of a heart rate per unit time toward a positive direction is larger. In addition, the following speed change quantity storage section 138 may store a larger change quantity as the change quantity toward a positive direction of the speed of causing the training image to follow the direction of the line of sight, in association with a case where the change quantity of a heart rate per unit time toward a negative direction is larger. The display control section 157 changes the speed of causing the training image stored in the training image storage section 140 to follow the direction of the line of sight, in accordance with the change quantity of the speed of causing the training image to follow the direction of the line of sight having received from the following speed change quantity extraction section 128. Then the display control section 157 controls the display section 160 to display the training image while causing the training image to follow the direction of the line of sight of the patient 200 at the changed speed.

According to the assisting apparatus 10 according to the present embodiment, when the patient 200 is feeling strong fear or anxiety, it becomes possible to perform: shortening the display time of a training image; decreasing the combination ratio of the training image to reduce the occupation area of the training image in the display area; or decreasing the superimposing degree between the training image and a non-training image. Accordingly, it becomes possible to restrain the occurrence of the patient 200 having an attack such as panic attack, while automatically subjecting the patient 200 to a suitable training image.

FIG. 7 shows one example of a data structure of the display ratio storage section 132 according to the present embodiment. The display ratio storage section 132 stores the change quantity of the display ratio of the training image displayed by the display section 160, in association with the physical state of the patient 200. The change quantity of the display ratio may be a change quantity of a display time, a combination ratio, and a superimposing degree for a training image, for example. For example, the display ratio storage section 132 stores the change quantity of the display ratio of the training image, in association with the change in expression of the patient 200 and the motion of the patient 200 as the physical state of the patient 200. Specifically, the display ratio storage section 132 stores the change quantity of the display ratio, in association with the change in expression of the patient 200 (i.e. motion of closing his eyes, motion of turning his eyes away, a smiling face, etc). Likewise, the display ratio storage section 132 stores the change quantity of the display ratio, in association with the motion of the patient 200 (e.g. the motion of the patient 200 lurching, the motion of looking down, the motion of trembling, the motion of swallowing the spit, the motion of shaking his head, or the like respectively).

For example, when the patient 200 performs the motion of closing his eyes, the fear or anxiety felt by the patient 200 is large, and so the display ratio storage section 132 may store the change quantity indicating to decrease the display time by 10 seconds in association with the motion of closing the eyes. When receiving from the display ratio extraction section 122 the change quantity of the display time stored in the display ratio storage section 132 in association with the motion of closing the eyes, the display control section 157 displays the training image on the display section 160 by decreasing the display time by 10 seconds. On the other hand, the display ratio storage section 132 may store the change quantity indicating to increase the display time by 10 seconds in association with a case where the patient 200 is smiling. Further, the display ratio storage section 132 may associate the change quantity of a predetermined combination ratio with the motion of closing the eyes. When receiving from the display ratio extraction section 122 the change quantity of the combination ratio stored in the display ratio storage section 132 in association with the motion of closing the eyes, the display control section 157 performs the display on the display section 160 by changing the combination ratio between a non-training image and a training image, according to the received change quantity of the combination ratio.

FIG. 8 shows one example of a data structure of the display ratio storage section 132 according to the present embodiment. The display ratio storage section 132 stores the change quantity of the display ratio of the training image in association with the biological information of the patient 200 as the physical state. For example, the display ratio storage section 132 may store the change quantity of the display ratio of a display time, a combination ratio, a superimposing degree, or the like, respectively in association with information indicating existence of perspiration, information indicating nonexistence of perspiration, and information indicating that the blood pressure of the patient 200 has exceeded a predetermined value or the like which are biological information of the patient 200. Specifically, the display ratio storage section 132 may store, in association with the biological information that the patient 200 exhibits when feeling fear or anxiety, the change quantity yielding a smaller display ratio than in the case where the patient 200 is not feeling fear or anxiety. For example, the display ratio storage section 132 may store, in association with a case where the blood pressure of the patient 200 has exceeded a predetermined value, the change quantity indicating to decrease the display time of the training image by 10 seconds.

FIG. 9 shows one example of a data structure of the display ratio storage section 132 according to the present embodiment. The display ratio storage section 132 stores the change quantity of the display ratio of the training image, in association with the change quantity per unit time of the biological information of the patient 200 as the physical state. For example, in association with the change quantity of the number of times of blinks per unit time calculated by the physical state analysis section 112 as a result of comparison between the number of times of blinks per unit time when the patient 200 is not looking at a training image and the number of times of blinks per unit time when the patient 200 is looking at a training image, the display ratio storage section 132 may store a change quantity yielding a smaller display ratio of the training image as the change quantity of the number of times of blinks per unit time toward a positive direction gets larger. For example, the display ratio storage section 132 may store the change quantity indicating to decrease the display time of the training image by 10 seconds, in association with the change quantity of the number of times of blinks per unit time of the patient 200 has increased by 50 times. Since the number of times of blinks per minute for a human person is usually 15 to 20 times, if the number of times of blinks per unit time has increased by 50 times, the patient 200 is judged to be undergoing fear or anxiety more when he is looking at a training image than when he is looking at a non-training image.

FIG. 10 shows one example of a data structure of the following speed change quantity storage section 138 according to the present embodiment. The following speed change quantity storage section 138 stores the change quantity of the display ratio of the training image in association with the change quantity per unit time of the biological information of the patient 200 as the physical state. For example, in association with the change quantity of the number of times of blinks per unit time calculated by the physical state analysis section 112 as a result of comparison between the number of times of blinks per unit time when the patient 200 is not looking at a training image and the number of times of blinks per unit time when the patient 200 is looking at a training image, the following speed change quantity storage section 138 may store the change quantity yielding a slower speed of causing the training image to follow as the change quantity of the number of times of blinks per unit time toward a positive direction gets larger. For example, the display ratio storage section 132 may store the change quantity indicating to decrease the speed of causing the training image to follow the direction of the line of sight of the patient 200 by 10 cm/second, in association with a case where the change quantity of the number of times of blinks per unit time of the patient 200 has increased by 30 times. Since the number of times of blinks per minute for a human person is usually 15 to 20 times, if the number of times of blinks per unit time has increased by 30 times, the patient 200 is judged to be undergoing fear or anxiety more when he is looking at a training image than when he is looking at a non-training image. Additionally, it is also possible to store information indicating to coercively stop causing the training image to follow the line of sight of the patient 200, in association with a case where the change quantity of the number of times of blinks per unit time has increased by 50 times, which is considered that the patient 200 is undergoing excessive fear or anxiety.

Figure 11:
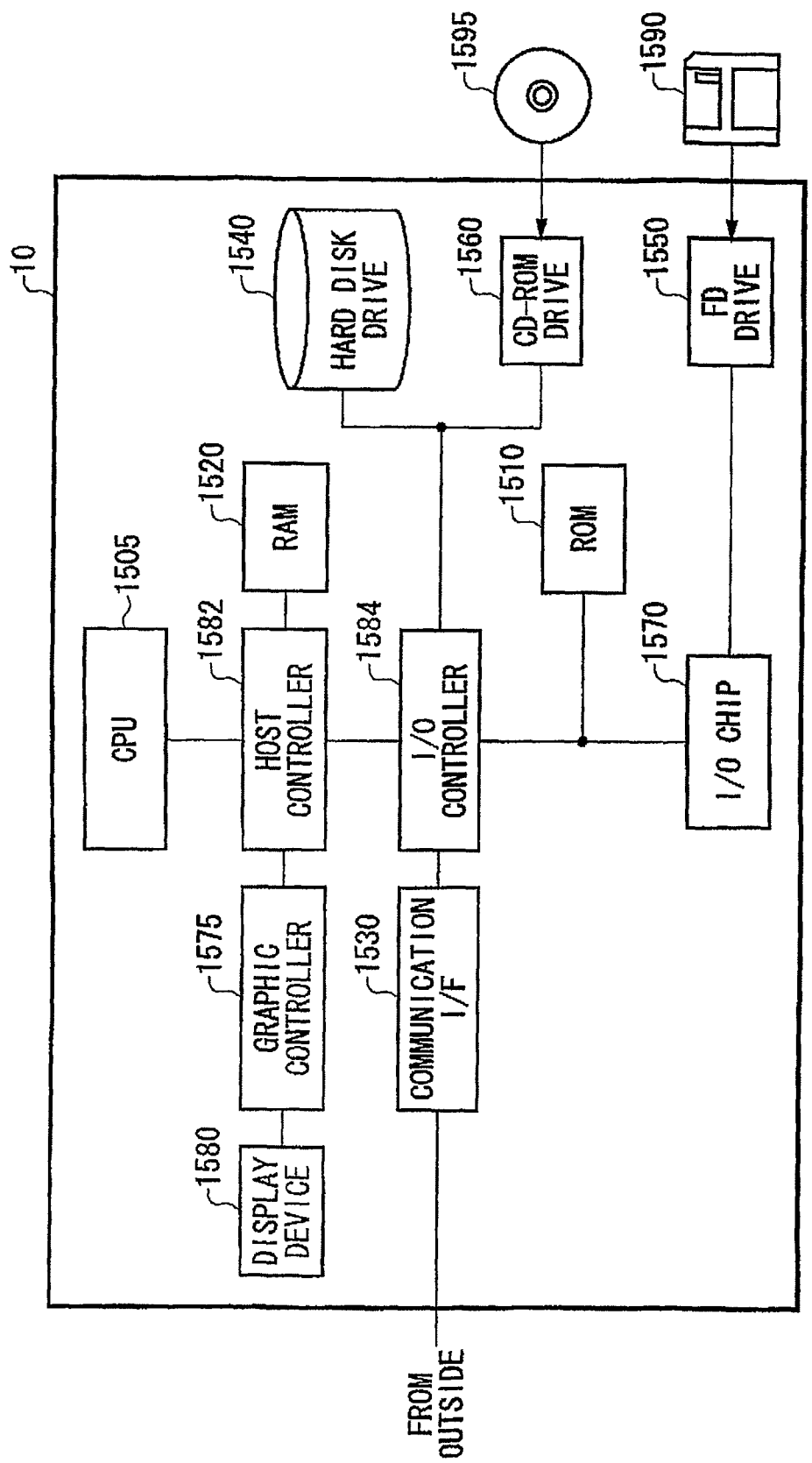
FIG. 11 is a block diagram showing a hardware configuration of the mental illness treatment assisting apparatus 10.

FIG. 11 shows one example of a hardware configuration of the assisting apparatus 10 according to the present embodiment. The assisting apparatus 10 according to the present embodiment includes a CPU periphery having a CPU 1505, a RAM 1520, a graphic controller 1575 and a display device 1580 which are connected through a host controller 1582 each other, an input/output unit having a communication interface 1530, a hard disk drive 1540 and a CD-ROM drive 1560 which are connected to the host controller 1582 through an input/output controller 1584 and a legacy input/output unit having a ROM 1510, a flexible disk drive 1550 and an input/output chip 1570 which are connected to the input/output controller 1584.

The host controller 1582 connects the RAM 1520 to the CPU 1505 and the graphic controller 1575 which access the RAM 1520 with a high transfer rate. The CPU 1505 operates according to the programs stored in the ROM 1510 and the RAM 1520 to control each unit. The graphic controller 1575 acquires image data generated on a frame buffer provided in the RAM 1520 by the CPU 1505 or the like and displays the same on the display 1580. Alternatively, the graphic controller 1575 may include therein a frame buffer for storing image data generated by the CPU 1505 or the like.

The input/output controller 1584 connects the host controller 1582 to the communication interface 1530, the hard disk drive 1540 and the CD-ROM drive 1560 which are relatively high-speed input/output units. The communication interface 1530 communicates with the other device through a network. The hard disk drive 1540 stores the program and data used by the CPU 1505 in the assisting apparatus 10. The CD-ROM drive 1560 reads the program or data from the CD-ROM 1595 and provides the same to the hard disk drive 1540 through the RAM 1520.

The ROM 1510, and the flexible disk drive 1550 and input/output chip 1570 which are relatively low-speed input/output units are connected to the input/output controller 1584. The ROM 1510 stores a boot program executed by the assisting apparatus 10 at activating the assisting apparatus 10 and a program depending on the hardware of the assisting apparatus 10. The flexible disk drive 1550 reads the programs or data from a flexible disk 1590 and provides the same to the hard disk drive 1540 through the RAM 1520. The input/output chip 1570 connects various input/output units through the flexible disk drive 1550 such as a parallel port, a serial port, a keyboard port and a mouse port.

A mental illness treatment assisting program (hereinafter simply "assisting program") provided to the hard disk drive 1540 through the RAM 1520 is in a recording medium, such as the flexible disk 1590, the CD-ROM 1595, an IC card or the like, and provided by the user. The assisting program is read from the recording medium, installed into the hard disk drive 1540 in the assisting apparatus 10 through the RAM 1520 and executed by the CPU 1505. The assisting program executed by being installed in the assisting apparatus 10 acts on the CPU 1505 or the like, to cause the assisting apparatus 10 to function as the image-capturing section 100, the biological information measurement section 105, the physical state acquiring section 110, the physical state analysis section 112, the biological information analysis section 114, the change quantity extraction unit 12, the image change quantity extraction section 120, the display ratio extraction section 122, the pressure change quantity extraction section 123, the sound change quantity extraction section 125, the vibration change quantity extraction section 126, the following speed change quantity extraction section 128, the change quantity storage unit 13, the image change quantity storage section 130, the display ratio storage section 132, the pressure change quantity storage section 133, the sound change quantity storage section 135, the vibration change quantity storage section 136, the following speed change quantity storage section 138, the training image storage section 140, the stimulus control unit 15, the sound change control section 150, the pressure control section 153, the image change control section 155, the vibration control section 156, the display control section 157, the stimulus presentation unit 16, the display section 160, the pressure playback section 163, the sound playback section 165, the vibration playback section 166, the electronic chart storage section 170, the presentation stimulus decision section 180, the disease case database 190, and the line-of-vision measurement section 195, as described from the drawings of FIG. 1 to FIG. 10.

In the above, the present invention has been described by way of an exemplary embodiment. However, it is needless to say that the technical scope of the present invention should not be limited by the above-described embodiment. In particular, the present invention has been described by taking an example of a mental illness treatment assisting apparatus in the above-described embodiment. However, the application of the training assisting apparatus, the training assisting method, and the training assisting program stored on a computer readable medium according to the present invention should not be limited to treatment of mental illnesses. It should be understood that those skilled in the art might make many changes and substitutions without departing from the spirit and the scope of the present invention. It is obvious from the appended claims that embodiments with such modifications also belong to the scope of the present invention.

The invention claimed is:

1. A training assisting apparatus for assisting an examinee in overcoming the examinee's worries by displaying a training image on a display section, comprising:
a physical state acquiring section including a sensor that acquires a heart rate of the examinee looking at the training image displayed on the display section; and
a display control section controls the display section which includes a display screen to display the training image such that a change quantity of at least one of a combination ratio of the training image, a superimposing degree of the training image and the number of simultaneously displayed training images toward a negative direction is larger, in association with a case where a change quantity per unit time of the heart rate, acquired by the physical state acquiring section, towards a positive direction is larger further comprising an examinee's line-of-sight measurement section that detects a direction of line of sight of the examinee, wherein
the display control section controls the display section to display the training image by causing the training image to follow the direction of the line of sight of the examinee such that a change quantity of the speed of causing the training image to follow the direction of the line of sight measured by the examinee's line-of-sight measurement section toward a negative direction is larger, in association with a case where a change quantity per unit time of the heart rate, acquired by the physical state acquiring section, towards a positive direction is larger;
and wherein the display control section controls the display section to display the training image by stopping causing the training image to follow the direction of line of sight of the examinee, in association with a case where a change quantity per unit time of the heart rate, acquired by the physical state acquiring section, exceeds a predetermined rate indicating that the examinee is feeling extraordinary fear.

2. The training assisting apparatus as set forth in claim 1, wherein
the display section displays the training image by inserting the training image to a motion picture that is not a training image.

3. The training assisting apparatus as set forth in claim 1, wherein the display section displays a combination of the training image and the non-training image.

4. The training assisting apparatus as set forth in claim 1, wherein the display section displays the training image by superimposing the training image on a non-training image.

5. The training assisting apparatus as set forth in claim 1, further comprising:
an image-capturing section that captures an image of the examinee looking at the training image displayed on the display section,
the physical state acquiring section acquires the motion of the examinee, by analyzing the image of the examinee captured by the image-capturing section, and
a display ratio extraction section extracts the change quantity of the display ratio of the training image in association with the motion of the examinee acquired by the physical state acquiring section.

6. The training assisting apparatus as set forth in claim 5, wherein the physical state acquiring section acquires the change quantity per unit time of the motion of the examinee, by analyzing the image of the examinee captured by the image-capturing section, and
the display ratio extraction section extracts the change quantity of the display ratio of the training image in association with the change quantity per unit time of the motion of the examinee acquired by the physical state acquiring section.

7. The training assisting apparatus as set forth in claim 1, further comprising:
a biological information measurement section that measures biological information of the examinee looking at the training image displayed on the display section, wherein
a display ratio storage section stores the change quantity of the display ratio of the training image displayed on the display section, in association with biological information of the examinee being the physical state of the examinee,
the physical state acquiring section acquires the biological information of the examiner measured by the biological information measurement section, and
a display ratio extraction section extracts the change quantity of the display ratio of the training image that the display ratio storage section stores in association with the biological information of the examinee acquired by the physical state acquiring section.

8. The training assisting apparatus as set forth in claim 7, wherein
the display ratio storage section stores the change quantity of the display ratio of the training image displayed on the display section, in association with a change quantity per unit time of the biological information of the examinee,
the physical state acquiring section acquires the change quantity per unit time of the biological information of the examinee measured by the biological information measurement section, and
the display ratio extraction section extracts the display ratio of the training image that the display ratio storage section stores in association with the change quantity per unit time of the biological information of the examinee acquired by the physical state acquiring section.

9. The training assisting apparatus as set forth in claim 1, further comprising:
- a sound playback section that plays back sound that corresponds to the training image displayed on the display section;
- a sound change quantity storage section that stores a change quantity of an information quantity of the sound played back by the sound playback section, in association with the physical state of the examinee;
- a sound change quantity extraction section that extracts the change quantity of the information quantity of the sound that the sound change quantity storage section stores in association with the physical state of the examinee acquired by the physical state acquiring section; and
- a sound change control section that changes the information quantity of the sound played back by the sound playback section, in association with the change quantity of the information quantity of the sound extracted by the sound change quantity extraction section.

10. The training assisting apparatus as set forth in claim 1, further comprising:
- a change quantity storage section that stores a larger change quantity as a change quantity of at least one of the combination ratio of the training image, the superimposing degree of the training image and the number of simultaneously displayed training images toward a negative direction, in association with a case where a change quantity per unit time of the heart rate of the examinee, acquired by the physical state acquiring section, toward a positive direction is larger; and
- an extraction section that extracts the change quantity of at least one of the combination ratio of the training image, the superimposing degree of the training image and the number of simultaneously displayed training images that the change quantity storage section stores in association with the heat rate of the examinee acquired by the physical state acquiring section, wherein
- the display control section controls the display section to display the training image, in accordance with the change quantity of at least one of the combination ratio of the training image, the superimposing degree of the training image and the number of simultaneously displayed training images extracted by the extraction section.

11. A training assisting apparatus for assisting an examinee in overcoming the examinee's worries by displaying a training image, comprising:
- a display section that displays the training image on a display screen;
- an image-capturing section that captures an image of the examinee looking at the training image displayed on the display section;
- an examinee's line-of-sight measurement section that detects a direction of line of sight of the examinee based on the image of the examinee captured by the image-capturing section; and
- a display control section that controls the display section to display the training image on the display screen by causing the training image to follow the direction of the line of sight of the examinee measured in the examinee's line-of-sight measurement section;
- a physical state acquiring section including a sensor that acquires, as a physical state of the examinee looking at the training image displayed on the display section, at least one of a heart rate of the examinee and the number of times of blinks of the examinee;
- a following speed change quantity storage section that stores a larger change quantity as a change quantity of the speed of causing the training image to follow the direction of the line of sight toward a negative direction, in association with a case where a change quantity of the physical state of the examinee, acquired by the physical state acquiring section, per unit time toward a positive direction is larger; and
- a following speed extraction section that extracts the change quantity of the speed of causing the training image to follow the direction of the line of sight of the examinee that the following speed change quantity storage section stores in association with the physical state of the examinee acquired by the physical state acquiring section, wherein
- the display control section controls the display section to display the training image by causing the training image to follow the direction of the line of sight of the examinee, in accordance with the change quantity of the speed of causing the training image to follow extracted by the following speed extraction section, wherein
- the following speed change quantity storage section stores information indicating to display the training image without moving the training image, in association with a predetermined physical state indicating that the examinee is feeling extraordinary fear,
- the following speed change quantity extraction section extracts the information indicating to display the training image without moving the training image stored in the following speed change quantity storage section, if the physical state of the examine acquired by the physical state acquiring section is the predetermined physical state, and
- the display control section controls the display section to display the training image based on the information indicating to display the training image without moving the training image extracted by the following speed change quantity extraction section.

12. A training assisting method for assisting an examinee in overcoming the examinee's worries by displaying a training image, comprising:
using one or more processors to perform:
- a display step of displaying the training image on a display section;
- an image-capturing step of capturing an image of the examinee looking at the training image displayed on the display section;
- an examinee's line-of-sight measurement step of detecting a direction of line of sight of the examinee based on the image of the examinee captured in the image-capturing step; and
- a display control step of controlling the display section to display the training image by causing the training image to follow the direction of the line of sight of the examinee measured in the examinee's line-of-sight measurement step;
- a physical state acquiring step of acquiring, as a physical state of the examinee looking at the training image displayed on the display step, at least one of a heart rate of the examinee and the number of times of blinks of the examinee;
- a following speed change quantity storage step of storing a larger change quantity as a change quantity of the speed of causing the training image to follow the direction of the line of sight toward a negative direction, in association with a case where a change quantity of the physical state of the examinee, acquired by the physical state acquiring step, per unit time toward a positive direction is larger; and a following speed extraction step of extracting the change quantity of the speed of causing the training image to follow the direction of the line of sight of the examinee that the following speed change quantity storage step of storing in association with the physical state of the examinee acquired by the physical state acquiring step, wherein the display control step of controlling the display step of displaying the training image by causing the training image to follow the direction of the line of sight of the examinee, in accordance with the change quantity of the speed of causing the training image to follow extracted by the following speed extraction step, wherein the following speed change quantity storage step stores information indicating to display the training image without moving the training image, in association with a predetermined physical state indicating that the examinee is feeling extraordinary fear, the following speed change quantity extraction step extracts the information indicating to display the training image without moving the training image stored in the following speed change quantity storage step, if the physical state of the examine acquired by the physical state acquiring step is the predetermined physical state, and the display control step controls the display section to display the training image based on the information indicating to display the training image without moving the training image extracted by the following speed change quantity extraction step.

13. A non-transitory computer readable medium storing thereon a training assisting program for a training assisting apparatus that assists an examinee in overcoming the examinee's worries by displaying a training image, the training assisting program causes the training assisting apparatus to function as:

a display section that displays the training image;

an image-capturing section that captures an image of the examinee looking at the training image displayed on the display section;

an examinee's line-of-sight measurement section that detects a direction of line of sight of the examinee based on the image of the examinee captured by the image-capturing section; and a display control section that controls the display section to display the training image by causing the training image to follow the direction of the line of sight of the examinee;

a physical state acquiring section that acquires, as a physical state of the examinee looking at the training image displayed on the display section, at least one of a heart rate of the examinee and the number of times of blinks of the examinee;

a following speed change quantity storage section that stores a larger change quantity as a change quantity of the speed of causing the training image to follow the direction of the line of sight toward a negative direction, in association with a case where a change quantity of the physical state of the examinee, acquired by the physical state acquiring section, per unit time toward a positive direction is larger; and a following speed extraction section that extracts the change quantity of the speed of causing the training image to follow the direction of the line of sight of the examinee that the following speed change quantity storage section stores in association with the physical state of the examinee acquired by the physical state acquiring section, wherein the display control section controls the display section to display the training image by causing the training image to follow the direction of the line of sight of the examinee, in accordance with the change quantity of the speed of causing the training image to follow extracted by the following speed extraction section, wherein the following speed change quantity storage section stores information indicating to display the training image without moving the training image, in association with a predetermined physical state indicating that the examinee is feeling extraordinary fear, the following speed change quantity extraction section extracts the information indicating to display the training image without moving the training image stored in the following speed change quantity storage section, if the physical state of the examine acquired by the physical state acquiring section is the predetermined physical state, and the display control section controls the display section to display the training image based on the information indicating to display the training image without moving the training image extracted by the following speed change quantity extraction section.

* * * * *